(12) United States Patent
Boomer et al.

(10) Patent No.: US 8,014,573 B2
(45) Date of Patent: Sep. 6, 2011

(54) DIGITAL LIFE RECORDING AND PLAYBACK

(75) Inventors: David Inman Boomer, Hampden, ME (US); Clifton E. Grim, III, Seabrook, TX (US); Rex Edward Marzke, Houston, TX (US); Gary A. Ward, Seabrook, TX (US); John David Wilson, Houston, TX (US)

(73) Assignee: International Business Machines Corporation, Armonk, NY (US)

( * ) Notice: Subject to any disclaimer, the term of this patent is extended or adjusted under 35 U.S.C. 154(b) by 327 days.

(21) Appl. No.: 11/968,772

(22) Filed: Jan. 3, 2008

(65) Prior Publication Data

US 2009/0177679 A1    Jul. 9, 2009

(51) Int. Cl.
*G06K 9/00* (2006.01)

(52) U.S. Cl. ............................ 382/118; 382/115

(58) Field of Classification Search ................ 382/115, 382/118

See application file for complete search history.

(56) References Cited

U.S. PATENT DOCUMENTS

| | | |
|---|---|---|
| 6,301,370 B1 | 10/2001 | Steffens et al. |
| 7,024,681 B1 | 4/2006 | Fransman et al. |
| 7,454,019 B2 | 11/2008 | Williams |
| 7,551,755 B1 | 6/2009 | Steinberg et al. |
| 7,555,148 B1 | 6/2009 | Steinberg et al. |
| 7,561,723 B2 | 7/2009 | Goldberg |
| 7,564,994 B1 | 7/2009 | Steinberg et al. |
| 7,664,233 B1 | 2/2010 | Kirchmeier et al. |
| 2002/0184196 A1 | 12/2002 | Lehmeier et al. |
| 2002/0188453 A1* | 12/2002 | Hirschberg et al. ........... 704/270 |
| 2003/0077074 A1 | 4/2003 | Okamoto et al. |
| 2003/0163339 A1 | 8/2003 | Elliot |
| 2004/0024688 A1 | 2/2004 | Bi et al. |
| 2004/0049571 A1 | 3/2004 | Johnson et al. |
| 2004/0155981 A1 | 8/2004 | Ichifuji et al. |
| 2004/0180683 A1 | 9/2004 | Dennis et al. |
| 2004/0213437 A1 | 10/2004 | Howard et al. |
| 2004/0246127 A1* | 12/2004 | Junqua .................... 340/539.13 |
| 2005/0075097 A1* | 4/2005 | Lehikoinen et al. ....... 455/414.1 |
| 2005/0105779 A1 | 5/2005 | Kamei |

(Continued)

FOREIGN PATENT DOCUMENTS

EP    1475967 A1    11/2004

(Continued)

OTHER PUBLICATIONS

Article entitled "Lifeblog: A new Concept in Mobile Learning" by Hartnell-Young et al., dated 2005.*

(Continued)

*Primary Examiner* — Mahesh Dwivedi
(74) *Attorney, Agent, or Firm* — Yee & Associates, P.C.; John R. Pivnichny

(57) ABSTRACT

The illustrative embodiments described herein provide a computer implemented method, apparatus, and computer program product for managing data. A plurality of devices dynamically capture data associated with the daily activities of a person. The data is transmitted to a mobile device associated with the person. The data is processed and then stored into a cache of the mobile device. The data stored in the cache of the mobile device is uploaded into a repository mass store in response to interfacing the mobile device with the repository mass store. A selected data segment stored in the repository mass store is presented in response to receiving a request for the selected data segment.

17 Claims, 23 Drawing Sheets

U.S. PATENT DOCUMENTS

| | | | |
|---|---|---|---|
| 2005/0154682 A1 | 7/2005 | Taylor | |
| 2005/0162279 A1 | 7/2005 | Marshall et al. | |
| 2005/0180567 A1 | 8/2005 | Williams | |
| 2005/0182701 A1 | 8/2005 | Cheston et al. | |
| 2005/0207622 A1 | 9/2005 | Haupt et al. | |
| 2005/0216274 A1 | 9/2005 | Kim | |
| 2005/0250548 A1* | 11/2005 | White | 455/566 |
| 2005/0257241 A1* | 11/2005 | Faulkner et al. | 725/92 |
| 2005/0264412 A1 | 12/2005 | Levesque et al. | |
| 2005/0270178 A1 | 12/2005 | Ioli | |
| 2006/0020630 A1 | 1/2006 | Stager et al. | |
| 2006/0072811 A1 | 4/2006 | Porter et al. | |
| 2006/0089912 A1 | 4/2006 | Spagna et al. | |
| 2006/0098088 A1* | 5/2006 | Raghunath | 348/61 |
| 2006/0156417 A1 | 7/2006 | Choi | |
| 2006/0200541 A1 | 9/2006 | Wikman et al. | |
| 2006/0222244 A1 | 10/2006 | Haupt et al. | |
| 2007/0003113 A1 | 1/2007 | Goldberg | |
| 2007/0036395 A1 | 2/2007 | Okun | |
| 2007/0049984 A1* | 3/2007 | Osypka | 607/32 |
| 2007/0112852 A1 | 5/2007 | Sorvari et al. | |
| 2007/0118372 A1* | 5/2007 | Wise et al. | 704/235 |
| 2007/0124272 A1 | 5/2007 | DeCastra et al. | |
| 2007/0150517 A1* | 6/2007 | Malone | 707/104.1 |
| 2007/0228159 A1 | 10/2007 | Kashiwa et al. | |
| 2007/0296817 A1 | 12/2007 | Ebrahimi et al. | |
| 2008/0046352 A1 | 2/2008 | Jung et al. | |
| 2008/0046406 A1* | 2/2008 | Seide et al. | 707/3 |
| 2008/0071561 A1 | 3/2008 | Holcombe | |
| 2008/0130960 A1 | 6/2008 | Yagnik | |
| 2008/0159601 A1 | 7/2008 | Alberth et al. | |
| 2008/0253623 A1 | 10/2008 | Hauke | |
| 2009/0030952 A1* | 1/2009 | Donahue et al. | 707/203 |
| 2009/0049413 A1 | 2/2009 | Lehtovirta et al. | |
| 2009/0109286 A1* | 4/2009 | Ennis | 348/81 |

FOREIGN PATENT DOCUMENTS

| | | |
|---|---|---|
| JP | 2002297893 | 10/2002 |
| WO | WO99/49656 | 9/1999 |

OTHER PUBLICATIONS

Picard, "Tales from the Cryptographer—Security guru Bruce Schneier busts the myths of post-Sep. 11 safety measures", Jun. 2006, pp. 1-3, retrieved Sep. 14, 2007. http://www.schneier.com/news-019.html.

Ward, "Log your life via your phone", BBC News Online, Mar. 2004, pp. 1-3, retrieved Sep. 14, 2007. http://news.bbc.co.uk/2/hi/technology/3497596.stm.

Seward, "Sensor rise powers life recorders", BBC News Online, Aug. 2007, pp. 1-3, retrieved Sep. 14, 2007. http://news.bbc.co.uk/2/hi/technology/6968591.stm.

Carter, "personal life recorder", William Carter weblog, Sep. 2004, pp. 1, retrieved Sep. 14, 2007. http://interactive.usc.edu/members/will/archives/002470.php.

Fleming, "Computers 'could store entire life by 2026'", Dec. 2006, pp. 1, retrieved Jan. 2, 2008. http://www.telegraph.co.uk/core/Content/displayPrintable.jhtml;jsessionid=C3FA5I1NTKF....

Genuth, "Saving Your Life on a Hard Drive", Jun. 2006, pp. 1-6, TFOT, retrieved Jan. 2, 2008. http://www.tfot.info/articles.php?itemId=16/.

"Welcome", pp. 1, Streav, retrieved Jan. 2, 2008. http://streav.sourceforge.net/.

U.S. Appl. No. 12/277,804, filed Nov. 25, 2008, Grim, III et al.
U.S. Appl. No. 12/130,549, filed May 30, 2008, Grim, III et al.
U.S. Appl. No. 12/277,873, filed Nov. 25, 2008, Grim, III et al.
U.S. Appl. No. 12/347,156, filed Dec. 31, 2008, Grim, III et al.
U.S. Appl. No. 12/347,182, filed Dec. 31, 2008, Grim, III et al.

Yasuhiko, Naito, "A Role of Advanced Image Data Logger Systems in Marine Animal Studies", Coast Marine Science, vol. 30, No. 2, Feb. 21, 2006, pp. 407-413, Japan, retrieved from the Internet: URL: http://repository.dl.itc.u-tokyo.ac.jp/dspace/bitstream/2261/5663/1/KJ00004354639.pdf.

"Youtube—Broadcast Yourself" Internet Citation, XP002441767, retrieved from the Internet: URL: http://web.archive.org/web/20051001143606/http://ww.youtube.com.

Ting, J. S. L, et al, "A Dynamic RFID-Based Mobile Monitoring System in Animal Care Management Over a Wireless Network", Wireless Communications, Networking and Mobile Computing, 2007, WICOM 2007, International Conference on, IEEE, Piscataway, NJ, USA, Sep. 21, 2007, pp. 2085-2088.

Healey, Jennifer et al, "Startle Cam: A Cybernetic Wearable Camera", Wearable Computers, 1998. Digest of Papers, Second International Symposium in Pittsburgh, PA, USA, Oct. 19-20, 1998, Los Alamitos, CA, USA, IEEE Comput. Soc, US, Oct. 19, 1998, pp. 42-49.

Frederick, "Surveillance Video Face Recognition (SVFR)", dated Nov. 2007.

USPTO office action for U.S. Appl. No. 12/277,804 dated Jun. 1, 2010.
USPTO office action for U.S. Appl. No. 12/347,182 dated May 28, 2010.
USPTO office action for U.S. Appl. No. 12/347,156 dated Jun. 21, 2010.
USPTO Final Office Action for U.S. Appl. No. 12/347,156 dated Oct. 14, 2010.
USPTO Final Office Action for U.S. Appl. No. 12/347,182 dated Oct. 27, 2010.
USPTO office action for U.S. Appl. No. 12/347,156 dated Jan. 31, 2011.
USPTO office action for U.S. Appl. No. 12/347,182 dated Feb. 2, 2011.
USPTO Notice of allowance for U.S. Appl. No. 12/347,182 dated Apr. 20, 2011.

* cited by examiner

DIGITAL LIFE RECORDING AND PLAYBACK

BACKGROUND OF THE INVENTION

1. Field of the Invention

The present invention relates generally to an improved data processing system and in particular to a method and apparatus for processing data. Still more particularly, the present invention related to a computer implemented method, apparatus, and computer program product for digital life recording.

2. Description of the Related Art

Advancements in technology have drastically changed the way people do things. Gone are the days of printed encyclopedias. These paper based resources have been replaced by a plethora of information readily available on the World Wide Web. Instead of taking a roll of film to a photo shop to be developed, digital images are stored on computers, laptops, and even in digital photo frames. Additionally, because taking a digital picture does not cost anything, more digital photos are taken than was previously taken by conventional means. The photos represent memories of special or even obscure events. However, searching for a particular photo out of the hundreds or thousands of images stored on a computer is a difficult task. In addition, numerous events in our daily lives are never captured on film. Furthermore, photos do not capture the spoken words, feelings, or environmental factors associated with everyday activities.

Accordingly, there exists a need for a mechanism for dynamically capturing, storing, and presenting data associated with all aspects of daily activities in an efficient manner.

SUMMARY OF THE INVENTION

The illustrative embodiments described herein provide a computer implemented method, apparatus, and computer program product for managing data. A plurality of data capturing devices dynamically capture data associated with the daily activities of a person. The data is processed using a mobile device associated with the person. The data is stored into a cache of the mobile device. The data stored in the cache of the mobile device is uploaded into a repository mass store in response to interfacing the mobile device with the repository mass store. A selected data segment stored in the repository mass store is presented in response to receiving a request for the selected data segment.

BRIEF DESCRIPTION OF THE DRAWINGS

The novel features believed characteristic of the invention are set forth in the appended claims. The invention itself, however, as well as a preferred mode of use, further objectives and advantages thereof, will best be understood by reference to the following detailed description of an illustrative embodiment when read in conjunction with the accompanying drawings, wherein:

DETAILED DESCRIPTION OF THE PREFERRED EMBODIMENT

Figure 1:
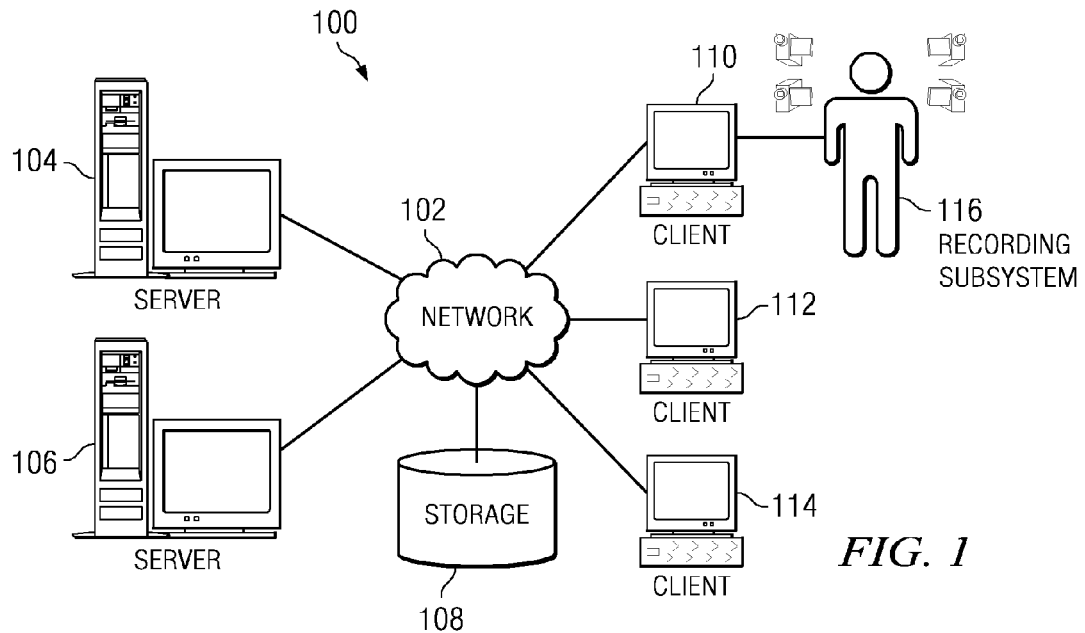
FIG. 1 is a pictorial representation of a network of data processing systems in which illustrative embodiments may be implemented.
Figure 2:
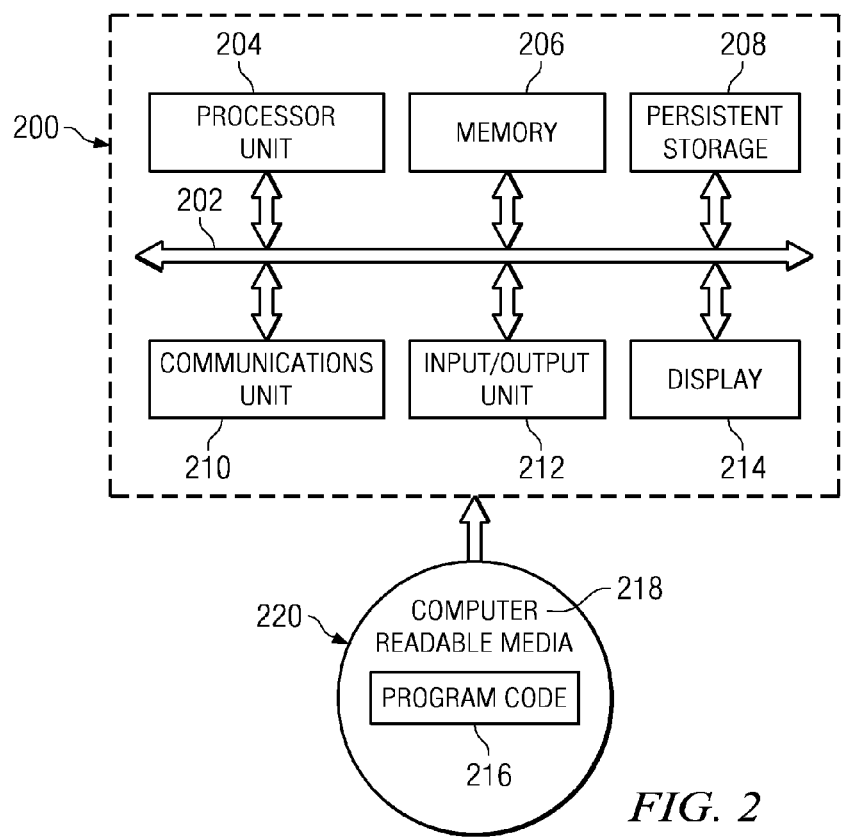
FIG. 2 is a block diagram of a data processing system in which illustrative embodiments may be implemented.

With reference now to the figures, and in particular with reference to FIGS. 1-2, exemplary diagrams of data processing environments are provided in which illustrative embodiments may be implemented. It should be appreciated that FIGS. 1-2 are only exemplary and are not intended to assert or imply any limitation with regard to the environments in which different embodiments may be implemented. Many modifications to the depicted environments may be made.

FIG. 1 depicts a pictorial representation of a network of data processing systems in which illustrative embodiments may be implemented. Network data processing system 100 is a network of computers in which embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. These clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. The illustrative embodiments may be implemented in a data processing system, such as clients 110, 112, and 114. Clients 110, 112, and 114 may use an Internet browser to communicate with server 104. Network data processing system 100 may include additional servers, clients, and other devices not shown.

The illustrative embodiments may be used as a digital life recorder for capturing still images, video, audio, biometric information and other types of data associated with the daily activities of a person. The activities may be recorded on a continuous basis or may be periodically captured. For example, FIG. 1 depicts a recording subsystem 116. Recording subsystem 116 receives data captured from a plurality of data capturing devices. The data capturing devices may include, but are not limited to, video cameras. The captured data is processed by a mobile device associated with the person and is stored as raw data within a cache of the mobile device. Upon interfacing with a repository mass store, such as client 110, the stored data within the cache of the mobile device is uploaded to the repository mass store. Client 110 manages the data within the repository mass store and presents the data in response to a user request. Additional details of recording subsystem 116 and the repository mass store will be described below.

Network 102 may be, without limitation, a local area network (LAN), wide area network (WAN), Internet, Ethernet, or Intranet. In this example, network 102 is the Internet, representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for different embodiments.

Turning now to FIG. 2, a diagram of a data processing system is depicted in accordance with an illustrative embodiment of the present invention. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multiprocessor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer readable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communications links or wireless transmissions containing the program code.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208 and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

The illustrative embodiments described herein provide a computer implemented method, apparatus, and computer program product for managing data. A plurality of data capturing devices dynamically captures data associated with the daily activities of a person. The data is processed using a mobile device associated with the person. As depicted in FIG. 1, clients 110, 112, and 114 may represent a mobile device. The data is stored into a cache of the mobile device. The data stored in the cache of the mobile device is uploaded into a repository mass store in response to interfacing the mobile device with the repository mass store. Interfacing may occur over a network, such as network 102 as shown in FIG. 1. Network 102 may comprise of a wired or wireless communication link. The repository mass store may be associated with a data processing system such as data processing system 200. A selected data segment stored in the repository mass store is presented in response to receiving a request for the selected data segment.

Figure 3:
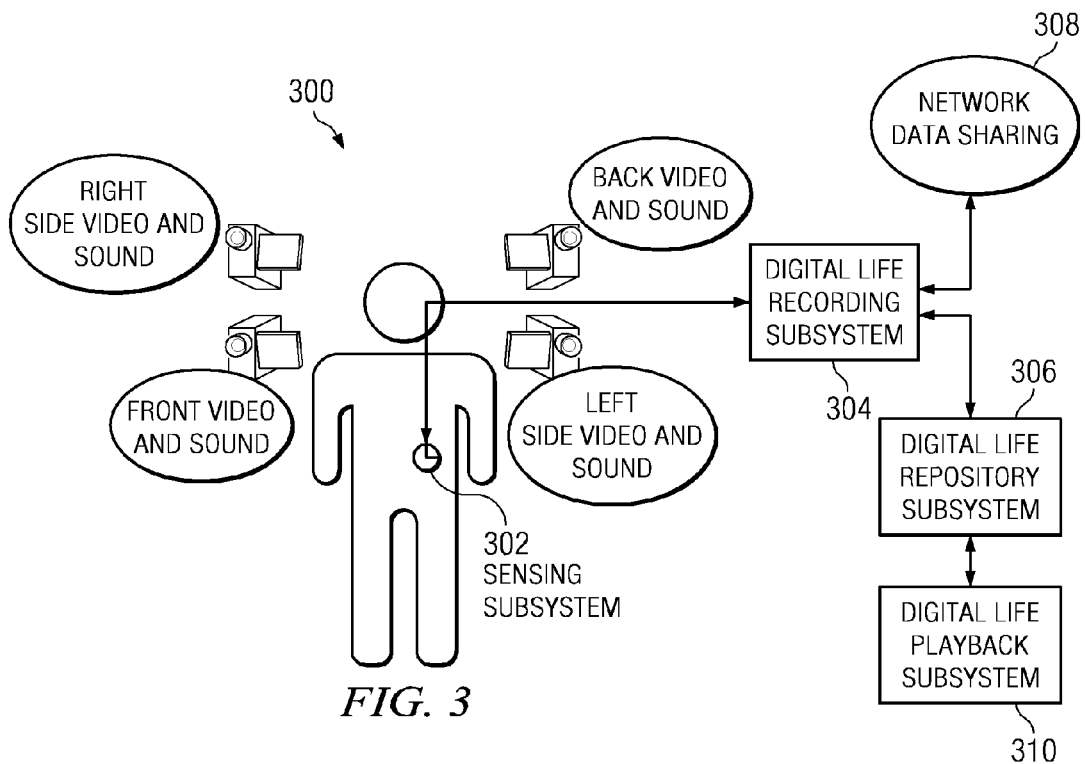
FIG. 3 is a diagram depicting components of a digital life recorder in accordance with an illustrative embodiment.

With reference now to FIG. 3, a diagram of components for a digital life recorder is depicted in accordance with an illustrative embodiment. In this example, digital life recording system 300 comprises of a sensing subsystem 302, a digital life recording subsystem 304, digital life repository subsystem 306, network data sharing 308, and digital life playback subsystem 310. Sensing subsystem 302 and digital life recording subsystem 304 may be implemented in a recording subsystem, such as recording subsystem 116 as shown in FIG. 1. Digital life repository subsystem 306, network data sharing 308, and digital life playback subsystem 310 may be implemented in a data processing system, such as data processing system 200 as shown in FIG. 2 and client 110 as shown in FIG. 1.

Sensing subsystem 302 comprises of data capturing devices for capturing data. The data capturing devices may comprise, for example, without limitation video capturing devices, audio capturing devices, biometric capturing devices, global positioning devices, environmental sensor devices, and other suitable devices for digital life recording. The data captured by the devices of subsystem 302 is referred to as digital life recording data.

As depicted in FIG. 3, the video capturing devices are positioned on the person to capture a 360 degree field of view around the person. Additionally, a set of audio capturing devices may be positioned around the person. A set of biometric sensors captures physiological data associated with the person, such as, but not limited to, the heart rate of the person. A set, as referenced herein, may be comprised of one or more objects. Global positioning system devices coupled to the person captures the location and the precise time that data is captured. A set of environmental sensor devices captures environmental variables, such as, but not limited to, temperature, wind speed, barometric pressure, and humidity. In addition, the set of environmental sensor devices may detect environmental hazards, such as, but not limited to, detecting the electric field, radiation, and carbon monoxide. Other data capturing devices that may associated with the person may include, but are not limited to, medical devices, cellular telephones, and radio-frequency identification devices.

The data capturing devices for capturing data may be hidden in common apparel such as glasses, a hat, clothing or jewelry. In another illustrative embodiment, some or all of the capturing devices may be medically implanted into the person's body.

Sensing subsystem 302 also comprises of a computer for processing the data captured by the devices into a raw data queue. Further details of sensing subsystem 302 are described in FIG. 4 below.

Sensing subsystem 302 transmits the raw data captured by the data capturing devices to digital life recording subsystem 304. Digital life recording subsystem 304 processes the raw data into a processed data queue and stores the data from the processed data queue into a daily cache of a mobile device associated with the person. The details of digital life recording subsystem 304 will be described in FIG. 5.

Digital life repository subsystem 306 manages the long term storage and cataloging of the information representing the person's "digital life" that accumulates over time. On a periodic basis, digital life repository subsystem 306 interfaces with digital life recording subsystem 304 and uploads data stored in the cache of the mobile device. Additionally, details of digital life repository subsystem 306 will be described in FIG. 6.

Network data sharing 308 is a component of digital life recording system 300. Network data sharing 308 provides functions, such as aggregating, organizing, formats, and attaching metadata to data acquired via public, inter-personal and intra-personal data sharing networks. The resultant aggregate is fed into digital life recording subsystem 304 in these examples. Network data sharing 308 is further described in FIG. 7 below.

Digital life playback subsystem 310 is responsible for the user interface that organizes and presents the information, stored in the digital life repository subsystem 306, to a user for review and further processing. Additional details of digital life playback subsystem 310 will be described in FIG. 8.

Figure 4:
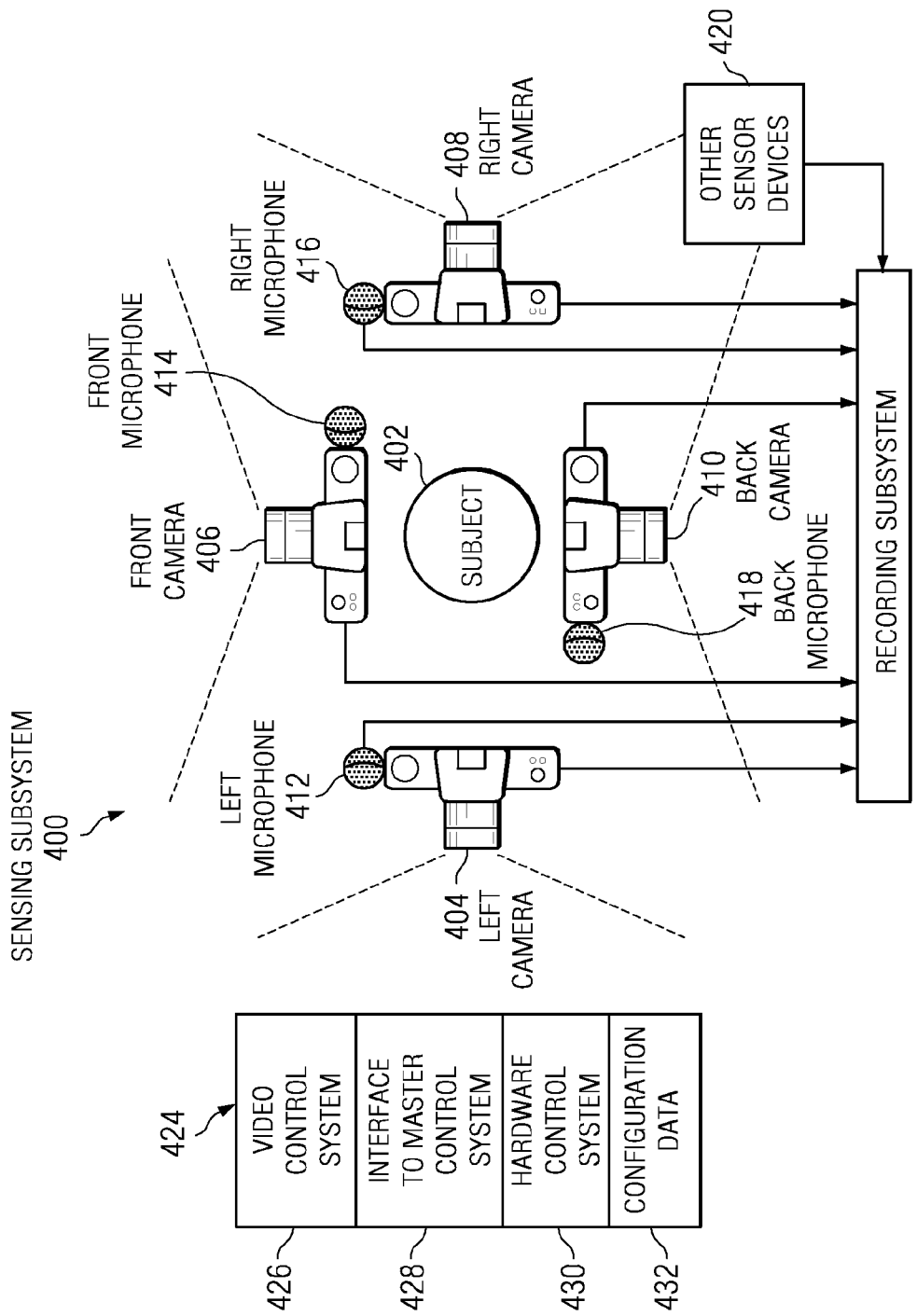
FIG. 4 is a diagram depicting components of a sensing subsystem in accordance with an illustrative embodiment.

With reference now to FIG. 4, a diagram of components in a sensing subsystem is depicted in accordance with an illustrative embodiment. Sensing subsystem 400 comprises of a plurality of data capturing devices associated with a person 402.

In this illustrative example, the data capturing devices comprises of a left camera 404, a front camera 406, a right camera 408, and a back camera 410. Additionally, a left microphone 412, a front microphone 414, a right microphone 416, and back microphone 418 are used for capturing audio data. A global positioning system 420 and other sensor devices 422 may also be associated with person 402. Other sensor devices 422 may include, but are not limited to, a set of biometric devices and a set of environmental sensor devices.

Data model 424 depicts the software components associated with managing sensing subsystem 400. Data model 424 comprises of a video control system 426, an interface to master control system 428, a hardware control system 430, and configuration data 432. The data captured by the data capturing devices is transmitted to a recording subsystem, as will be described below in FIG. 5.

Figure 5:
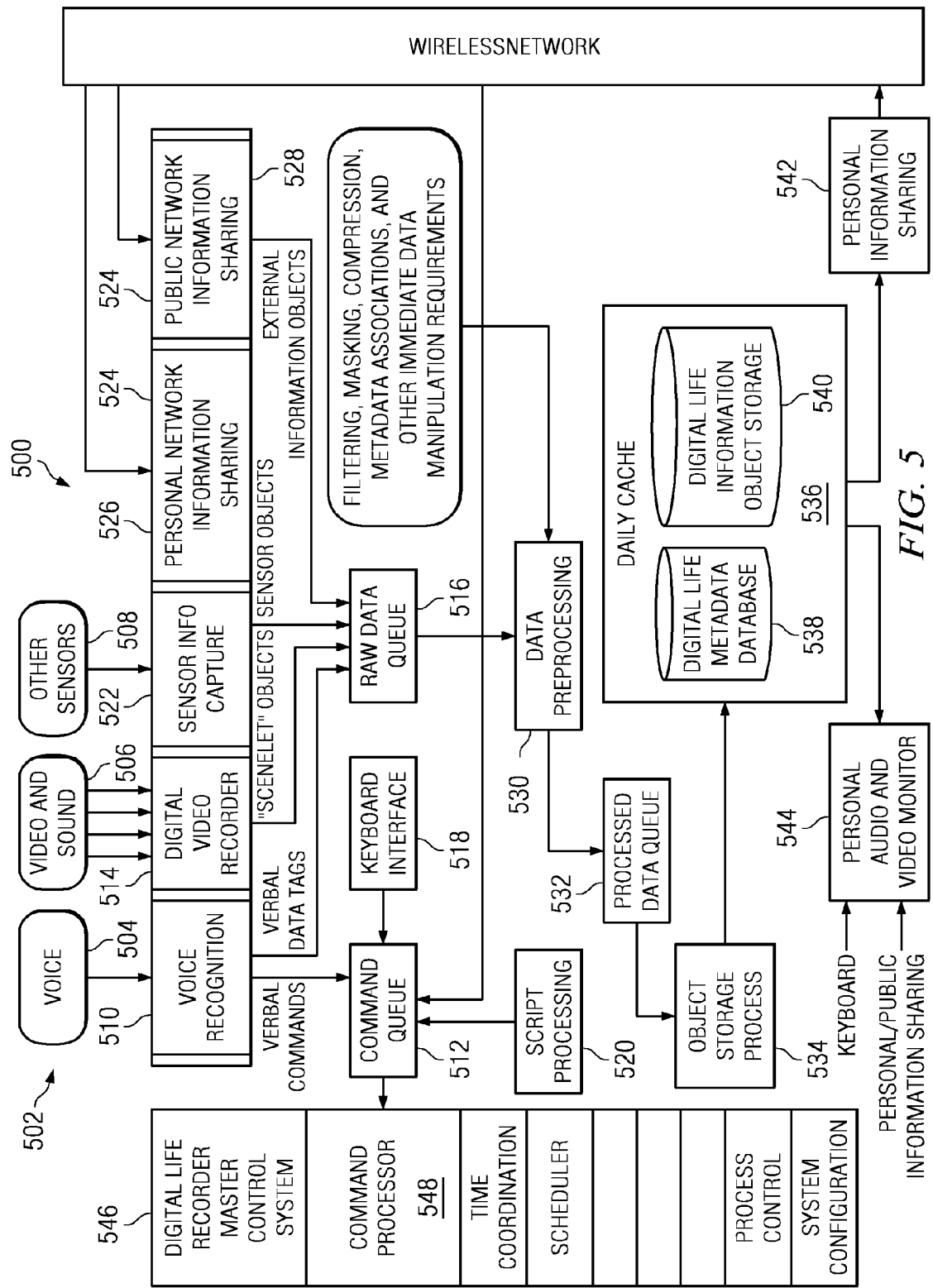
FIG. 5 is a block diagram illustrating the relationship between components of a sensing subsystem and the components of a recording subsystem in accordance with an illustrative embodiment.

FIG. 5 is a block diagram illustrating the data flow between components of a sensing subsystem and the components of a recording subsystem 500 in accordance with an illustrative embodiment. The components of recording subsystem 500 may be implemented in a data processing system, such as data processing system 200 as shown in FIG. 2.

Recording subsystem 500 processes inputs and commands from all the different sources and stores the data in a daily cache. In this illustrative example, recording subsystem 500 comprises of a voice recognition component 510, a command queue 512, a digital video recorder 514, a raw data queue 516, a keyboard interface 518, a script processing 520, a sensor information capture 522, a data preprocessing component 530, a processed data queue 532, an object storage process 534, and a daily cache 536.

Recording subsystem 500 receives input from sensing subsystem 502. Sensing subsystem 502 depicts inputs received from data capturing devices in accordance with an illustrative embodiment of a sensing subsystem, such as sensing subsystem 302 in FIG. 3. Sensing subsystem 502 is responsible for capturing video and sound, voice commands, time and location, environmental details like temperature, biometric information, and any other information that can be imagined to be useful and for which sensors exist. In this example, inputs captured by sensing subsystem 502 includes voice input 504, video and sound input 506, and input from other sensors 508.

Digital life recorder master control system 546 directs the control of sensing subsystem 502. Master control system 546 passes the captured data on to recording subsystem 500 for further processing.

Recording subsystem 500 sends data received from voice input 504 to voice recognition component 510. Voice recognition component 510 processes the data received from voice input 504 to interpret voice commands. The voice commands are forwarded to command queue 512. Command queue 512 may also receive other types of input, such as, but not limited to, input from a cellular phone (not depicted), keyboard interface 518, or inputs received from script processing 520. A script is a set of commands written in an interpreted language to automate certain application tasks. Command queue 512 sends commands to master control system 546. These commands are executed by a command processor 548. The commands can be used to get feedback through headphones and/or display and allows the user to control and configure the system in near real-time.

Recording subsystem 500 passes data from video and sound input 506 to digital video recorder 514. Digital video recorder 514 converts analog data to digital data and organizes the data into data segments. Digital video recorder 514 also takes in metadata from the data capturing devices. Metadata is data that describes the content, quality, condition, origin, and other characteristics of data. The metadata includes a timestamp and location captured by a global positioning system device, such as global positioning system 418 shown in FIG. 4.

The data segments are tagged with the timestamp and location of when and where each data segment was captured prior to sending the data segments to raw data queue 516. In addition, data is captured from other sensors 508 and processed by sensor information capture 522 prior to relaying the data to raw data queue 516.

Additionally, raw data queue 516 includes external information data gathered from a network data sharing component 524. Network data sharing component 524 aggregates, organizes, formats, and attaches metadata to data acquired via public, inter-personal and intra-personal data sharing networks. Network data sharing component 524 includes a personal network information sharing component 526 and a public network information sharing component 528. Network data sharing component 524 is described in more detail in FIG. 7 below.

Data preprocessing component 530 filters, masks, compresses, applies metadata associations, and processes other immediate data manipulation functions. Data preprocessing component 530 reads information from raw data queue 516 and passes the pre-processed data along to processed data queue 532. Recording subsystem 500 uses processed data queue 532 to temporarily store the data before passing the data along to the object storage process 534. Object storage process 534 places the data into daily cache 536. The data is placed into two separate databases within daily cache 536; digital life metadata database 538 and digital life information object database 540. Daily cache 536 has enough storage capacity to hold the captured data until recording subsystem 500 interfaces with a repository mass store.

Figure 7:
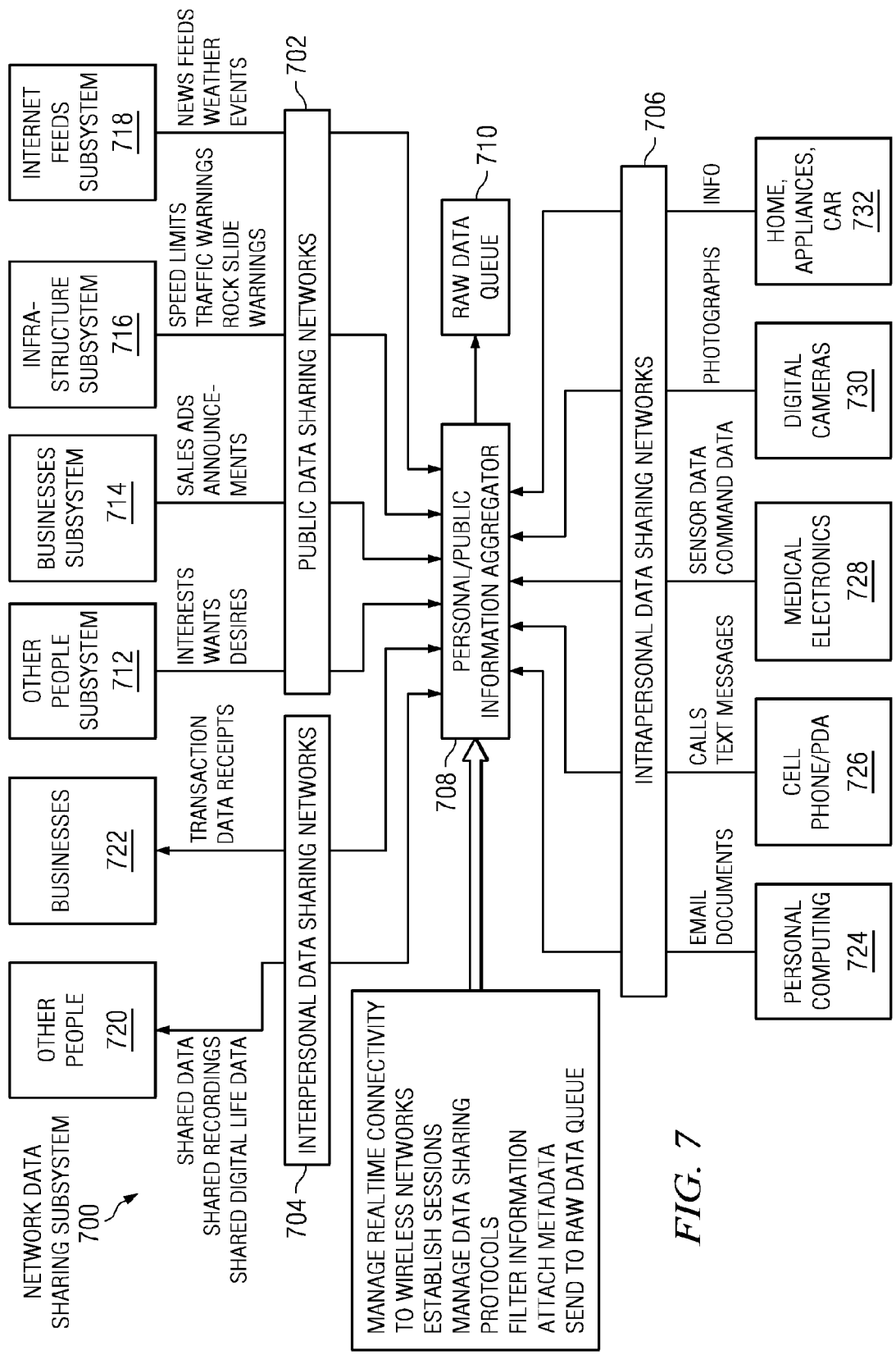
FIG. 7 is a block diagram illustrating the relationship between components of a network data sharing subsystem in accordance with an illustrative embodiment.

Recording subsystem 500 uses a personal information sharing subsystem 542, as will be further described in FIG. 7, to broadcast information from digital life metadata database 538 and digital life information object database 540, within daily cache 536, to authorized users via a wireless or Bluetooth network. Recording subsystem 500 also uses a personal audio and video monitor subsystem 544 to provide a user interface to the data in daily cache 536. Recording subsystem 500 provides a keyboard, which can be used to enter commands and access the user interface functions. Recording subsystem 500 also provides a method to describe and connect to network data sharing component 524.

Figure 6:
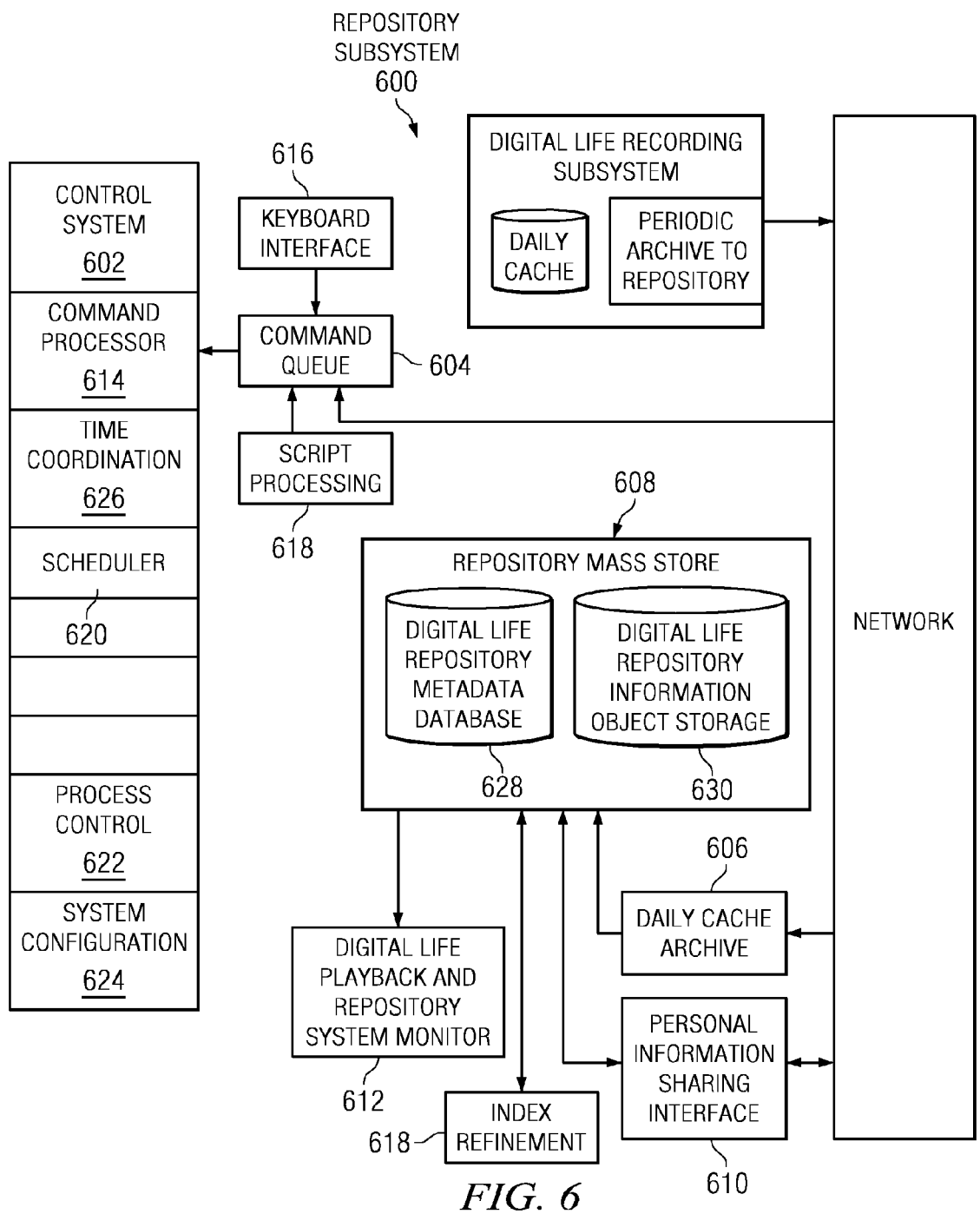
FIG. 6 is a block diagram illustrating the relationship between components of a repository subsystem in accordance with an illustrative embodiment.

With reference now to FIG. 6, a block diagram illustrating the relationship between a recording subsystem and the components of a repository subsystem is depicted in accordance with an illustrative embodiment. The recording subsystem may be, for example, recording subsystem 500 shown in FIG. 5. The components of repository subsystem 600 illustrated in FIG. 6 may be implemented in a data processing system, such as data processing system 200 as shown in FIG. 2.

Repository subsystem 600 includes a control system 602, a command queue 604, a network interface (not depicted), a relational storage means called the repository (repository database 608), personal information sharing interface 610, and an interface to the playback subsystem (Digital Life Playback and Repository System Monitor 612).

Control system 602 contains a command processor 614 which interprets and executes commands generated by either a keyboard interface 616, remote operation via the network, or scripts which are executed (script processing 618) according to a scheduler 620. In addition, control system 602 manages, processes and threads (process control 622, system configuration 624, and any time coordination 626 that might be required.

Recording subsystem 500, as shown in FIG. 5, interfaces with a network, such as network 102 shown in FIG. 1, to upload data stored in the daily cache to repository subsystem 600. Repository subsystem 600 interfaces to the network to download the daily cache archive 606 previously stored by the recording subsystem.

Repository subsystem 600 stores the data into repository database 608. Repository database 608 includes two databases, digital life repository metadata database 628 and digital life repository information object storage 630, for long term storage and use. Digital life repository information object storage 630 stores the captured life data objects. Digital life repository metadata database 628 stores metadata used to index and describe the actual captured information objects that the Digital Life Recording Subsystem acquires during the life recording process. Additionally, repository database 608 may include information obtained through personal information sharing interface 610. Additional details of the network data sharing subsystem are described in more detail in FIG. 7 below.

On an ongoing basis, the indexing information in digital life repository metadata database 628 may be enhanced and refined by processes that study the capture data in the repository and update the index information (Ongoing Data and Index Refinement 618). An example of the refinement process includes analyzing audio data within an object to recognize words associated with the captured object. These words are then used as part of a full text search capability where the identified words are used as index information that points to the data objects that contains those words.

An interface, such as digital life playback and repository system monitor 612, exists between repository subsystem 600 and a playback subsystem. Digital life playback and repository system monitor 612 allows the playback subsystem to access the data existing in repository database 608 based on various searching techniques. The playback subsystem manages displaying of the data to a user. Digital life playback and repository system monitor 612 also manages the status and manipulation of the repository subsystem 600. Additional details of a playback subsystem are described in more detail in FIG. 8 below.

With reference now to FIG. 7, a block diagram illustrating the relationship between components of a network data sharing subsystem is depicted in accordance with an illustrative embodiment. The components of network data sharing subsystem 700 illustrated in FIG. 7 may be implemented in a data processing system, such as data processing system 200 as shown in FIG. 2.

Network data sharing subsystem 700 includes public data sharing network 702, interpersonal data sharing network 704, intrapersonal data sharing network 706, and a personal/public information aggregator 708.

Public data sharing network 702 provides connectivity to information that is being locally broadcast as well as predefined Internet feeds. The system may be composed of wireless networks configured to connect automatically when detected. Hard networks may also be used to capture additional information.

Additionally, public data sharing network 702 captures nearby information, from other people broadcasting information about themselves, via the other people subsystem 712. This information might be information about their interests and desires. Public data sharing network 702 also captures business information from nearby business broadcasts, such as, but not limited to, sales and advertisements via the businesses subsystem 714.

Additionally, public data sharing network 702 captures public and private infrastructure broadcasts via the infrastructure subsystem 716. The public and private infrastructure information may include, but are not limited to, speed limits, traffic conditions/warnings, and weather condition warnings. Public data sharing network 702 supports any network connectivity that allows Internet access via the Internet Feeds subsystem 718. Internet Feeds subsystem 718 is used to receive web based information, such as, but not limited to, news, weather, entertainment, and sports results.

Interpersonal data sharing network 704 is more specific to the person being monitored than is public data sharing network 702. Interpersonal data sharing network 704 does not receive broadcasts. Instead, interpersonal data sharing network 704 negotiates connections with Other People 720 and Businesses 722 to receive transaction oriented information for recording. For example, transaction information associated with transactions that occur between businesses and the person are recorded. The transaction information may include information about purchases, such as, but not limited to, price, model numbers, serial numbers, warranties, and receipts. Information shared from other people's digital life recording system is captured using a subsystem, such as other people 720.

Intrapersonal data sharing network 706 aggregates personal information about the person's life for recording. The personal information may be aggregated from a plurality of sources including, but not limited to, personal computing 724, cell phone/personal digital assistants (pda) 726, medical electronics 728, digital cameras 730, and home appliances/car 732. The information captured from personal computing 724 may include, but is not limited to, emails, computer files, computer-based communications like instant messages or voice over IP (VOIP). Bluetooth or other wireless/wired connectivity may be used for interfacing the data to the digital life recorder.

Intrapersonal data sharing network 706 may also capture cell phone conversations and PDA usage from cell phone/PDA 726 using Bluetooth connectivity or other transmission means. Additionally, intrapersonal data sharing network 706 may record the command and data associated with medical electronics 728. Images may also be captured from digital cameras 730. Digital cameras 730 include cameras that are not already associated with the sensing subsystem. Other data may include information associated with home appliances/car 732.

Personal/public information aggregator 708 aggregates, organizes, formats, and attaches metadata to data acquired via public data sharing network 702, interpersonal data sharing network 704, and intrapersonal data sharing network 706. The resultant aggregate is fed into the raw data queue 710 of a recording subsystem, such as recording subsystem 500 in FIG. 5.

Figure 8:
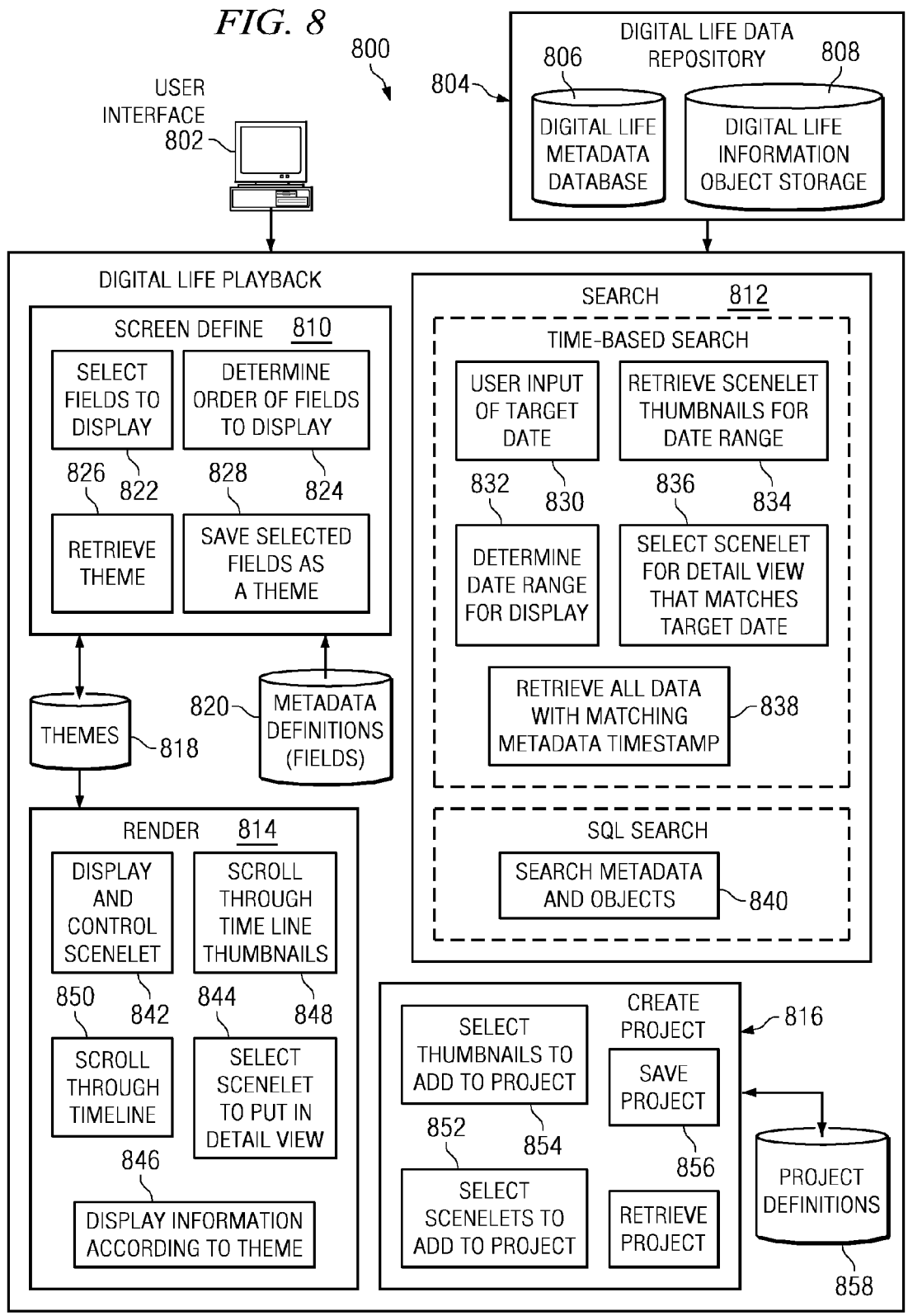
FIG. 8 is a block diagram illustrating the components of a playback subsystem in accordance with an illustrative embodiment.

Turning now to FIG. 8, a block diagram illustrating the components of a playback subsystem is depicted in accordance with an illustrative embodiment. The components of playback subsystem 800 illustrated in FIG. 8 may be implemented in a data processing system, such as data processing system 200 as shown in FIG. 2.

In this example, playback subsystem 800 comprises of several subsystems, such as, but not limited to, screen define subsystem 810, search subsystem 812, render subsystem 814, and create project subsystem 816. Additionally, playback subsystem 800 includes a user interface 802 associated with the digital life recording system. User interface 802 may be used to organize and present information stored in a data repository, such as repository database 608 shown in FIG. 6. Playback subsystem 800 interfaces with digital life data repository 804. Digital life data repository 804 includes digital life metadata database 806 and digital life information object storage database 808. Digital life data repository 804 may be similarly implemented as repository database 608 shown in FIG. 6.

Screen define subsystem 810 provides an interface to receive user inputs, such as, but not limited to, selecting the type of information a user wants to view. The type of information may include, but is not limited to, video information, sound information, temperature sensor information, or any of the other information captured by the recording system or network data sharing system. The definition for these types of information and their mapping to the digital life data database is managed through the metadata definitions database 820. The information can be organized on user interface 802 and then saved in a themes database 818 using the function save selected fields as a theme (block 828). Saved themes may be retrieved from themes database 818 using the retrieve theme (block 826) functionality. Other functionality provided by screen define subsystem 810 may include, but is not limited to, computer usable program code that allows a user to select fields to display (block 822), and to determine order of fields to display (block 824).

Search subsystem 812 allows a user to input a date/time range to select the data that the user wants to view (block 830). Search subsystem 812 determines the initial date range to display on the user interface (block 832) prior to searching digital life data repository 804. Search subsystem 812 retrieves the scenelet thumbnails from digital life information object storage database 808 for the time slices within the date range (block 834). A scenelet is a snippet of a scene. Additional details about a selected scenelet may be viewed (block 836).

For all non-video information or metadata that is to be displayed on the screen, such as, but not limited to, sound and temperature, similar searching is performed and summaries retrieved for each time slice (block 838). Detailed information for the requested date/time will also be retrieved. Similarly, a generic searching capability is provided that uses standard search language queries, such as Structured Query Language (SQL), to allow access to any aspect of the digital life data repository 804 (block 840).

Render subsystem 814 is used to render the information retrieved, using search subsystem 812, on user interface 802. As stated above, the layout of user interface 802 is defined using screen define subsystem 810 and stored in themes database 818. Render subsystem 814 provides functionality to display, manipulate, and control a scenelet (block 842), select a scenelet for a detail view (block 844), display information according to theme (block 846), scroll through time line of thumbnails (block 848), and scroll through time line (block 850).

Create project subsystem 816 is used to support the creation of a saved set of information found in digital life data repository 804. A user may, using user interface 802, select either scenelets (block 852) or thumbnails (block 854), from the render subsystem 814 and save the group of items as a project (block 856) in a project definitions database 858. Additionally, previously saved projects may be retrieved from the project definitions database 858 using user interface 802.

Figure 9:
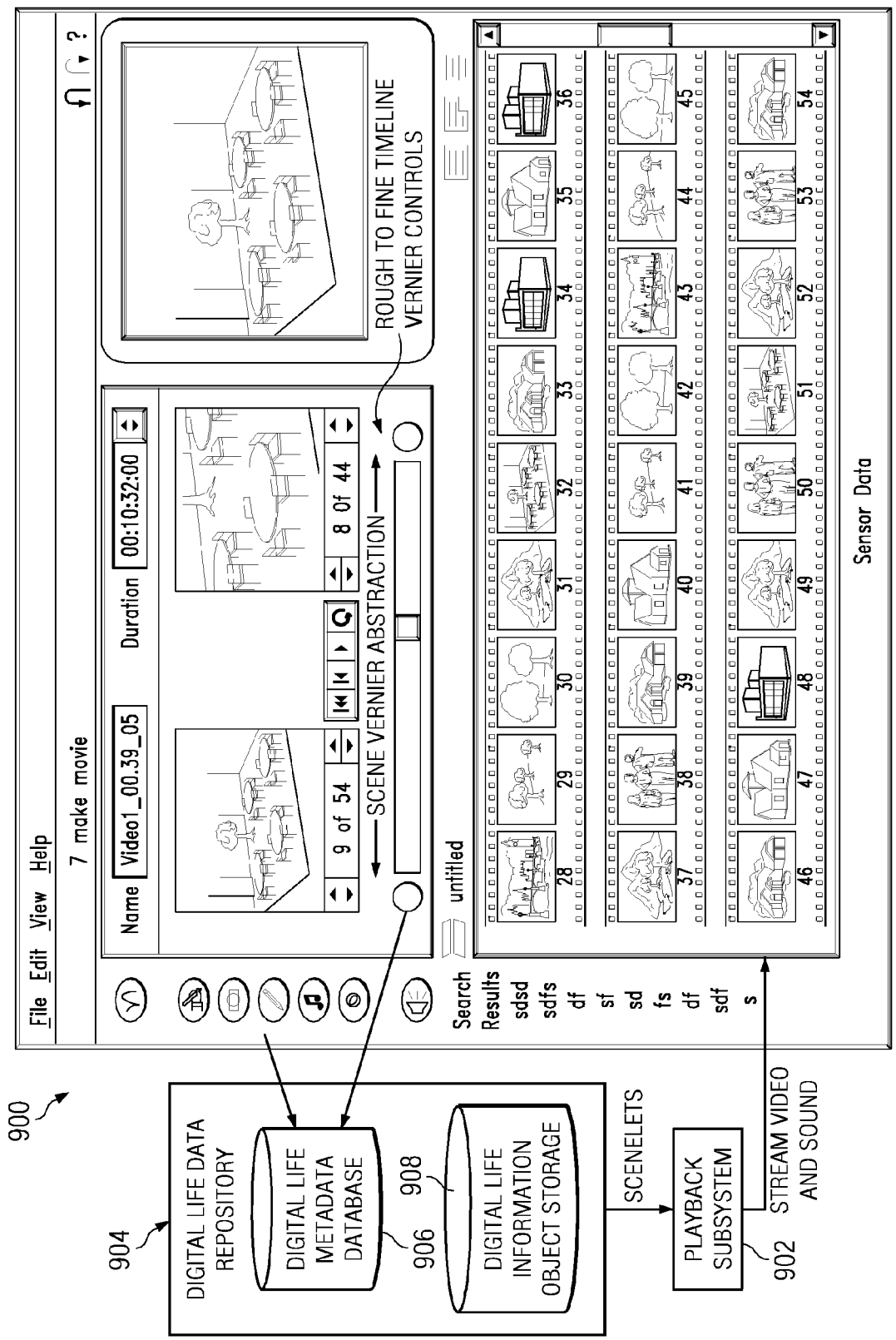
FIG. 9 is a diagram depicting a user interface associated with the playback subsystem in accordance with an illustrative embodiment.

With reference now to FIG. 9, a user interface 900 associated with a playback subsystem 902 is depicted in accordance with an illustrative embodiment. Playback subsystem 902 uses data acquired from a digital life data repository 904. Digital life data repository 904 contains digital life metadata database 906 and digital life information object storage database 908. Digital life data repository 904 may be similarly implemented as repository database 608 shown in FIG. 6.

The results associated with a search are depicted on the left hand side of user interface 900. Additionally, user interface 900 provides a mechanism for adjusting the timeline vernier. The timeline vernier controls the precision of time. Thus, a user can adjust from a rough timeline vernier to a more precise/fine timeline vernier. Scenelets associated with a selected result is presented in the bottom half of user interface 900.

Figure 10:
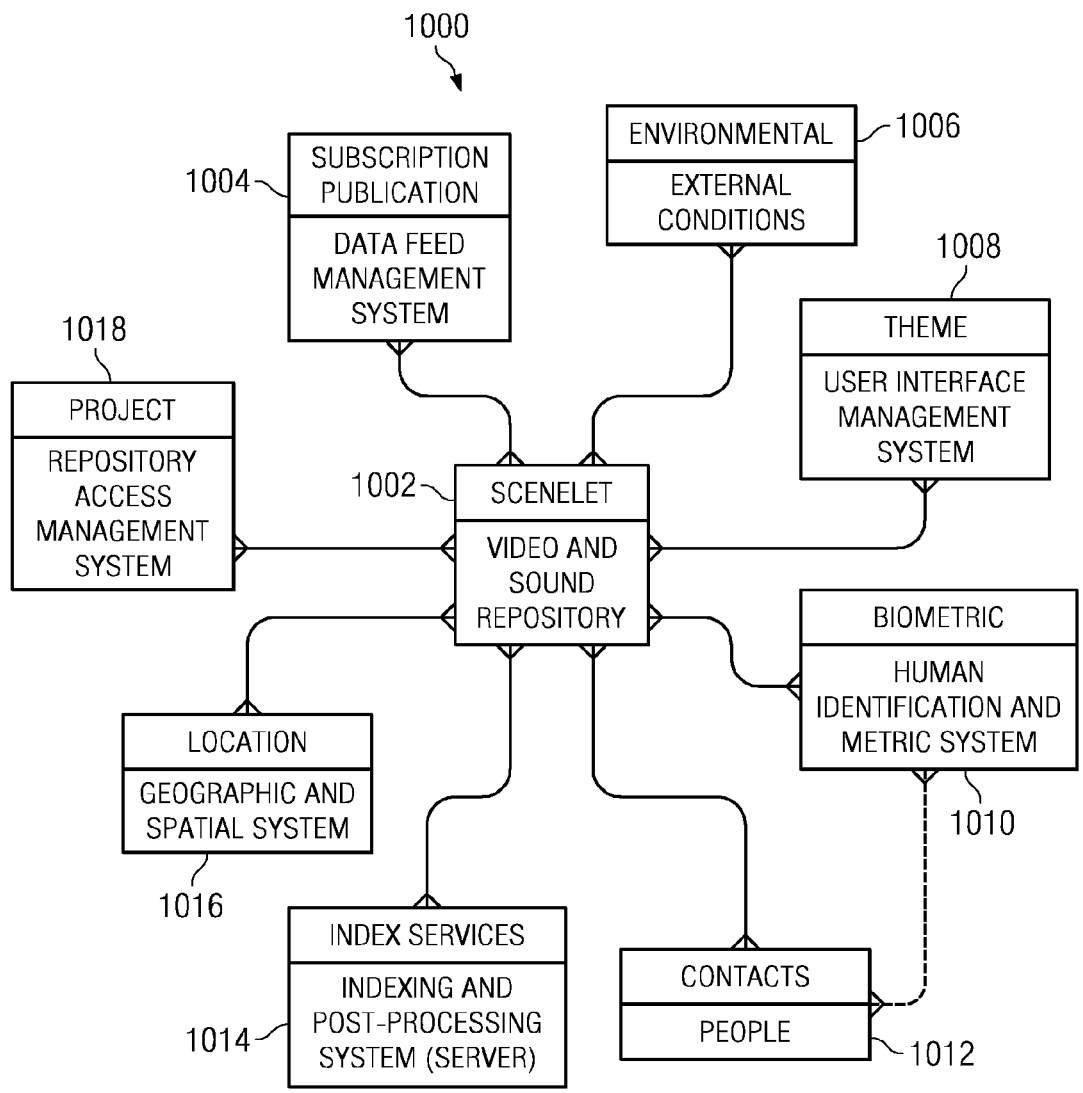
FIG. 10 is a diagram depicting a data model in accordance with an illustrative embodiment.

FIG. 10 is a diagram of a data model in accordance with an illustrative embodiment. Digital life conceptual data model 1000 may include, but is not limited to, the following subsystems: scenelet 1002, subscription/publication 1004, environmental 1006, theme 1008, biometric 1010, contacts 1012, index services 1014, location 1016, and project 1018.

Scenelet 1002 organizes and manages the image and sound files. Subscription/publication 1004 manages the external data feeds into and out of the digital life system, such as digital life recording system 300 shown in FIG. 3. Environmental 1006 captures and manages environmental characteristics related to the scenelet data. Theme 1008 allows users to customize and manage their digital life system interfaces and experiences. Biometric 1010 captures and manages biometric information associated with human contacts within the scenelets. Contacts 1012 is a repository of known contacts. Index services 1014 provides post processing capability to further analyze and categorize scenelet data. Location 1016 captures and manages specific location related details during a scenelet. Project 1018 provides an access management system that allows users to customize data retrieval.

Figure 11:
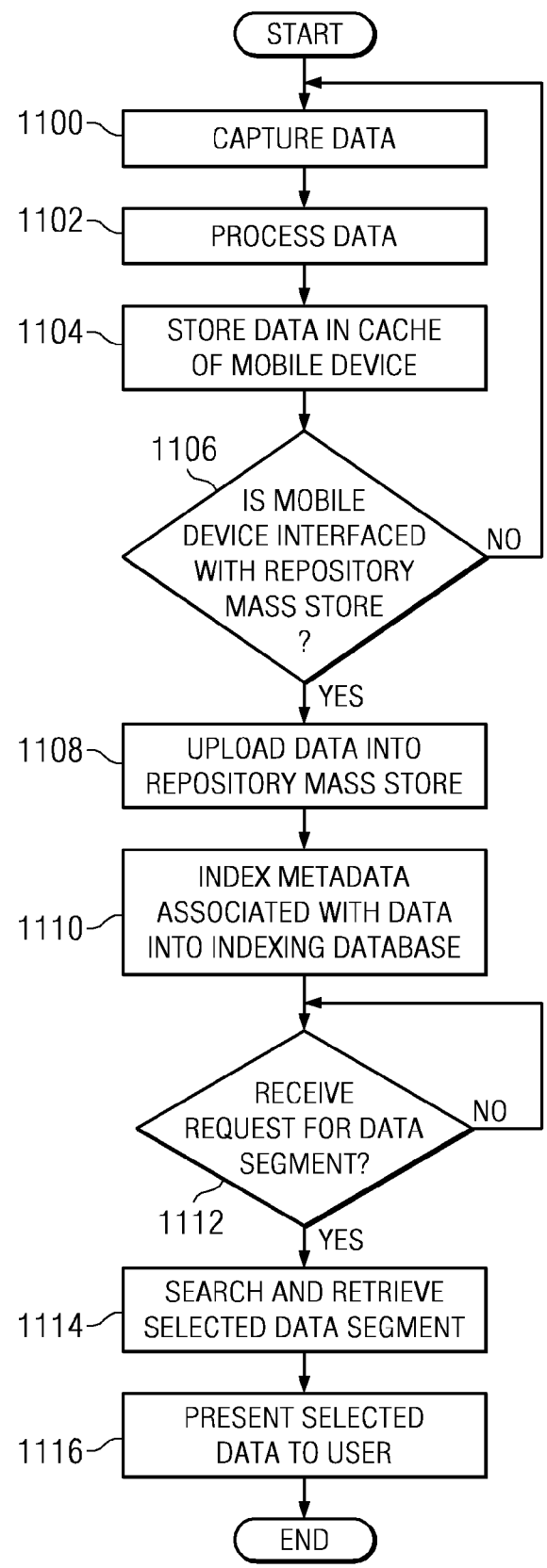
FIG. 11 is a high-level flowchart illustrating a process for capturing, storing, and presenting data in accordance with an illustrative embodiment.

With reference now to FIG. 11, a high-level flowchart is presented illustrating a process for capturing, storing, and presenting data in accordance with an illustrative embodiment. The process illustrated in FIG. 11 may be implemented in a digital life recording system, such as digital life recording system 300 shown in FIG. 3.

The process begins by capturing data associated with daily activities of a person using data capturing devices (step 1100). The captured data is processed by a mobile device associated with the person (step 1102). The data is then stored in a cache of the mobile device (step 1104). The process monitors the mobile device to determine when the mobile device is interfaced with a repository mass store (step 1106). Interfacing may occur when the mobile device is in the vicinity of the repository mass store and connection is established via a wireless transmission link. Interfacing may also occur when the mobile device is docked to a repository mass store. The process continues the process of capturing (step 1100), processing (step 1102), and storing (step 1104) the data until a determination is made that the mobile device is interfaced with a repository mass store.

In response to interfacing the mobile device to a repository mass store, the process uploads the data stored in the cache of the mobile device into the repository mass store (step 1108). Metadata associated with the data, is indexed into an indexing database (step 1110). The process monitors for a request, from a user, to retrieve a selected data segment (step 1112). In response to receiving a request for a selected data segment, the process performs a search and retrieves the selected data segment from the repository mass store (step 1114). The process presents the selected data segment to the user (step 1116), with the process terminating thereafter.

Figure 12:
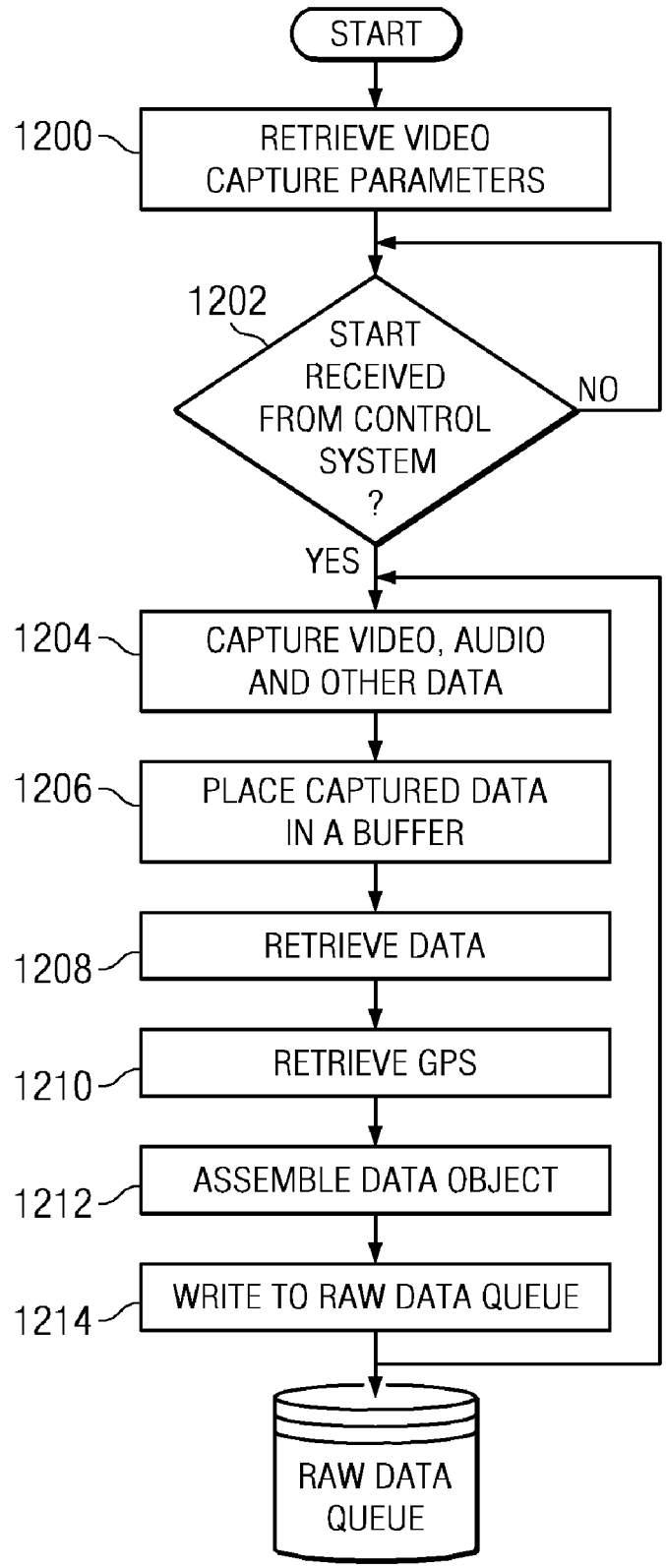
FIG. 12 is a flowchart illustrating a process for capturing life data in accordance with an illustrative embodiment.

With reference now to FIG. 12, a flowchart illustrating a process for capturing life data is depicted in accordance with an illustrative embodiment. The process illustrated in FIG. 12 may be implemented in a digital life recording system, such as digital life recording system 300 shown in FIG. 3.

The process begins by retrieving the video capture parameters (step 1200). The process monitors for start request from the control system (step 1202). In response to receiving a start request from the control system, the process captures the video, audio, and other data from the data capturing devices associated with a person (step 1204). The captured data is placed in a buffer for temporary storage (step 1206). The process retrieves data from the buffer (step 1208). Additionally, the process retrieves data associated with a global positioning system device (step 1210). The process assembles a data object by associating the data associated with a global positioning system device with the data retrieved from the buffer (step 1212). The process writes the data object to a raw data queue (step 1214). The process repeats steps 1204-1214 until all the data in the buffer is written to the raw data queue.

Figure 13:
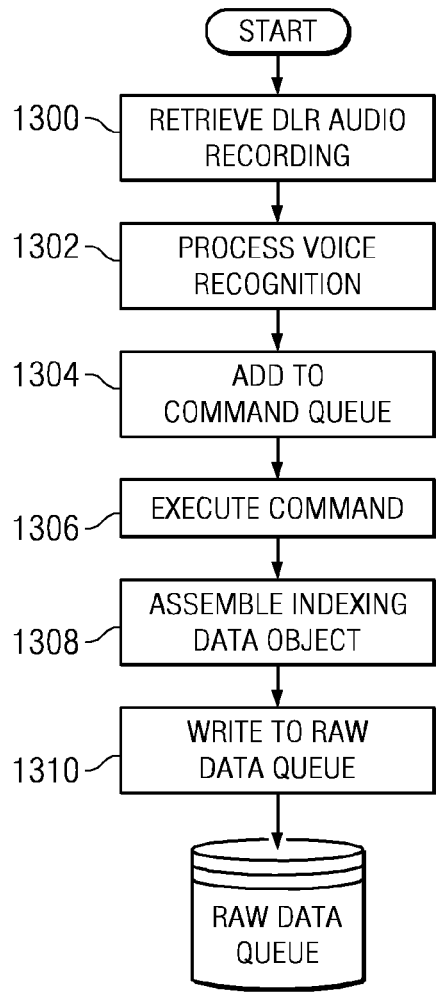
FIG. 13 is a flowchart illustrating a process for using voice commands for tagging life data objects in accordance with an illustrative embodiment.

FIG. 13 is a flowchart of a process for improving the indexing of the stored data by tagging life data objects in accordance with an illustrative embodiment. The process illustrated in FIG. 13 may be implemented in a digital life recording system, such as digital life recording system 300 shown in FIG. 3.

The process begins by retrieving audio recording associated with a digital life recording system (step 1300). The audio recording is processed through a voice recognition subsystem to interpret voice commands (step 1302). The process adds the voice commands to a command queue (step 1304). Commands may also be added to the command queue using a mouse or keyboard. The tagging command includes a timestamp and a descriptive text index tag string. The process executes the commands stored in the command queue (step 1306). The process assembles the descriptive text index tag string and timestamp into an indexing data object. (step 1308). The process writes the tagged data object to a raw data queue (step 1310) for later placement into the metadata database, with the process terminating thereafter.

Figure 14:
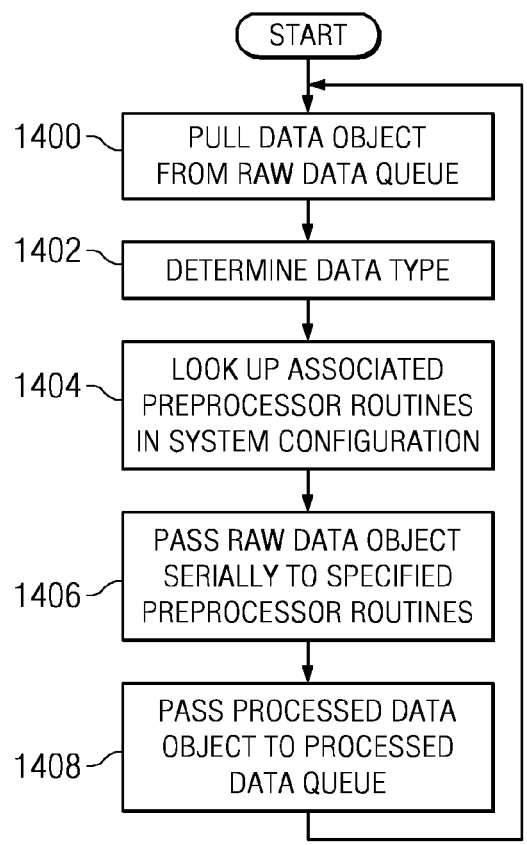
FIG. 14 is a flowchart illustrating a process for preprocessing raw recorded data in accordance with an illustrative embodiment.

FIG. 14 is a flowchart of a process for preprocessing raw recorded data in accordance with an illustrative embodiment. The process illustrated in FIG. 14 may be implemented in a digital life recording system, such as digital life recording system 300 shown in FIG. 3.

The process begins by pulling a data object from the raw data queue (step 1400). The process determines the data type of pulled data object (step 1402). The process looks up the associated preprocessor routines in system configuration (step 1404). The process passes the raw data object serially to the specified preprocessor routines (step 1406). The specified preprocessor routines return the processed data object to the process. The process then passes the processed data object to a processed data queue (step 1408). The process loops and repeats steps 1400-1408.

Figure 15:
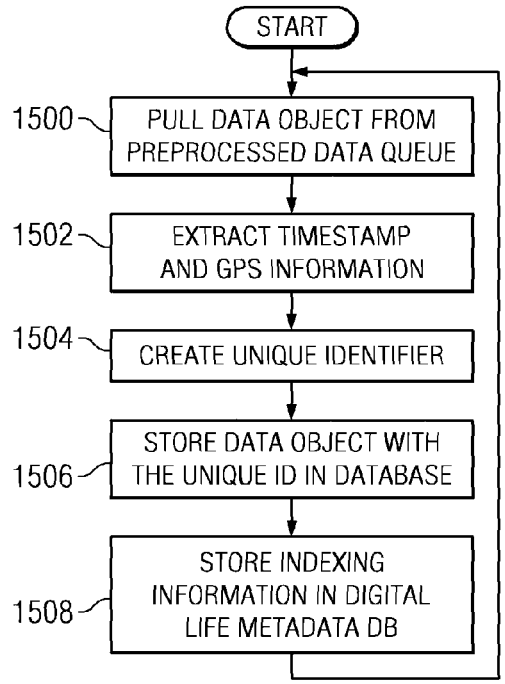
FIG. 15 is a flowchart illustrating a process for creating a unique identifier for indexing and storing data objects in accordance with an illustrative embodiment.

FIG. 15 is a flowchart of a process for creating a unique identifier for indexing and storing data objects in accordance with an illustrative embodiment. The process illustrated in FIG. 15 may be implemented in a digital life recording system, such as digital life recording system 300 shown in FIG. 3.

The process begins by pulling a data object from the pre-processed data queue (step 1500). The process extracts the timestamp and global positioning system (GPS) information from the data object (step 1502). The process creates a unique identifier for identifying the data object (step 1504). The process then stores the data object along with the unique identifier in a digital life information object storage database (step 1506), such as digital life repository information object storage 630 shown in FIG. 6. The process stores indexing information, such as, but not limited to, a timestamp, global positioning system information, the unique identifier, and the physical location of where the data object is stored in the digital life information object storage database, in a digital life repository metadata database (step 1508), such as digital life repository metadata database 628 shown in FIG. 6. The process loops and repeats steps 1500-1508.

Figure 16:
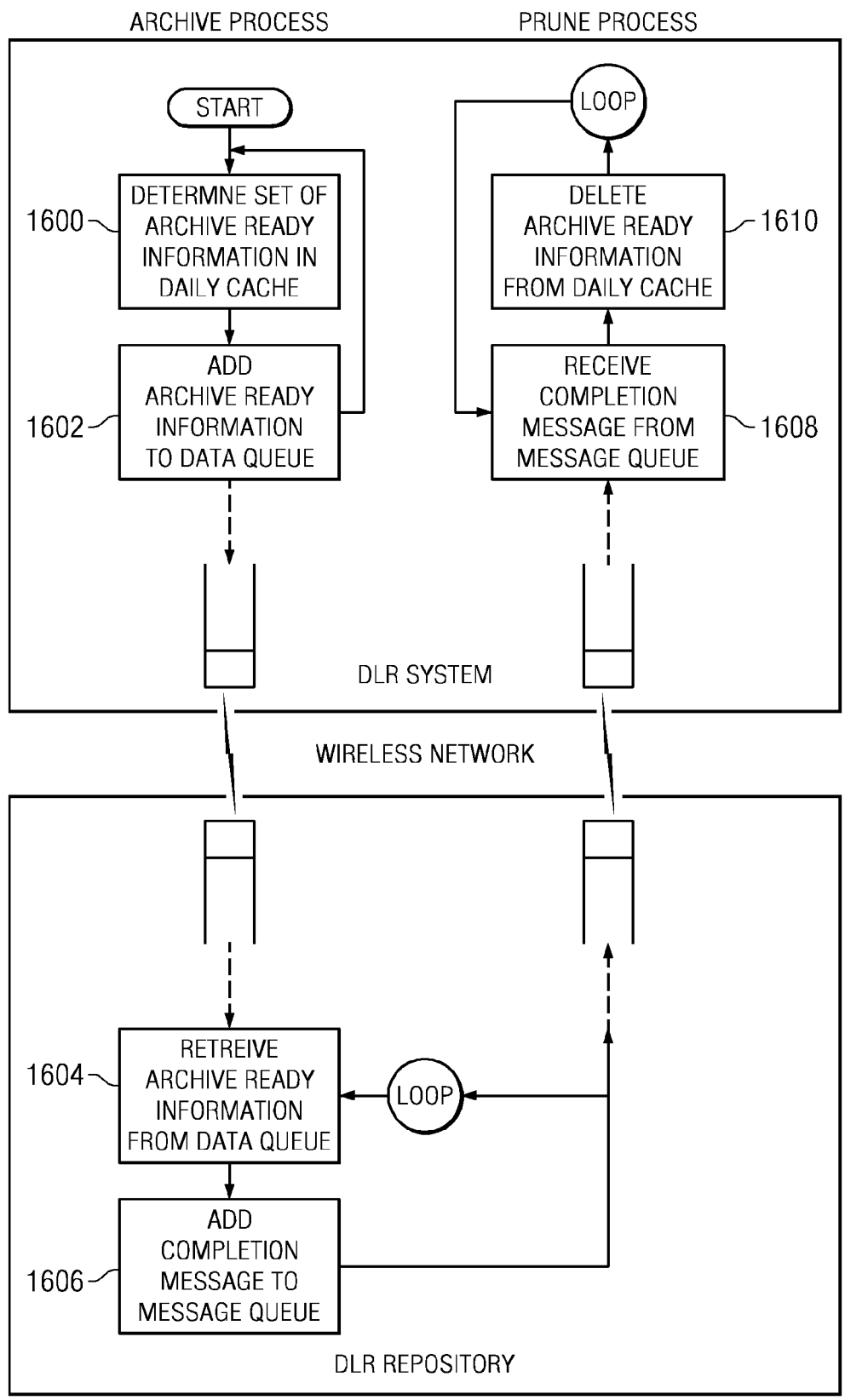
FIG. 16 is a flowchart illustrating a process for archiving data objects in accordance with an illustrative embodiment.

FIG. 16 is a flowchart of a process for archiving data objects in accordance with an illustrative embodiment. The process illustrated in FIG. 16 may be implemented in a digital life recording system, such as digital life recording system 300 shown in FIG. 3.

The process begins by determining a set of archive ready information stored in the daily cache of a mobile device (DLR system) (step 1600). The mobile device is associated with a person being recorded. The archive ready information comprises of the stored data objects, metadata, and other data associated with the captured data. The process adds the set of archive ready information to a data queue (step 1602). The process loops and repeats the steps of determining (step 1600) and adding (step 1602) archive ready information to a data queue until there is no more archive ready information.

In response to the mobile device interfacing with a repository mass store, the process retrieves the set of archive ready information from the data queue (step 1604). The process inserts the set of archive ready information into the repository mass store, such as repository database 608 shown in FIG. 6. The process then adds a completion message to a message queue (step 1606). The process loops and repeats the steps of retrieving (step 1604) and inserting (step 1606) archive ready information into the repository mass store until all archive ready information is stored in the repository mass store.

The process receives completion messages from the message queue (step 1608). In response to receiving the completion messages from the message queue, the process deletes the set of archive ready information from the daily cache (step 1610). The process loops and repeats the steps of receiving completion messages from the message queue (step 1608) and deleting the set of archive ready information from the daily cache (step 1610).

Figure 17:
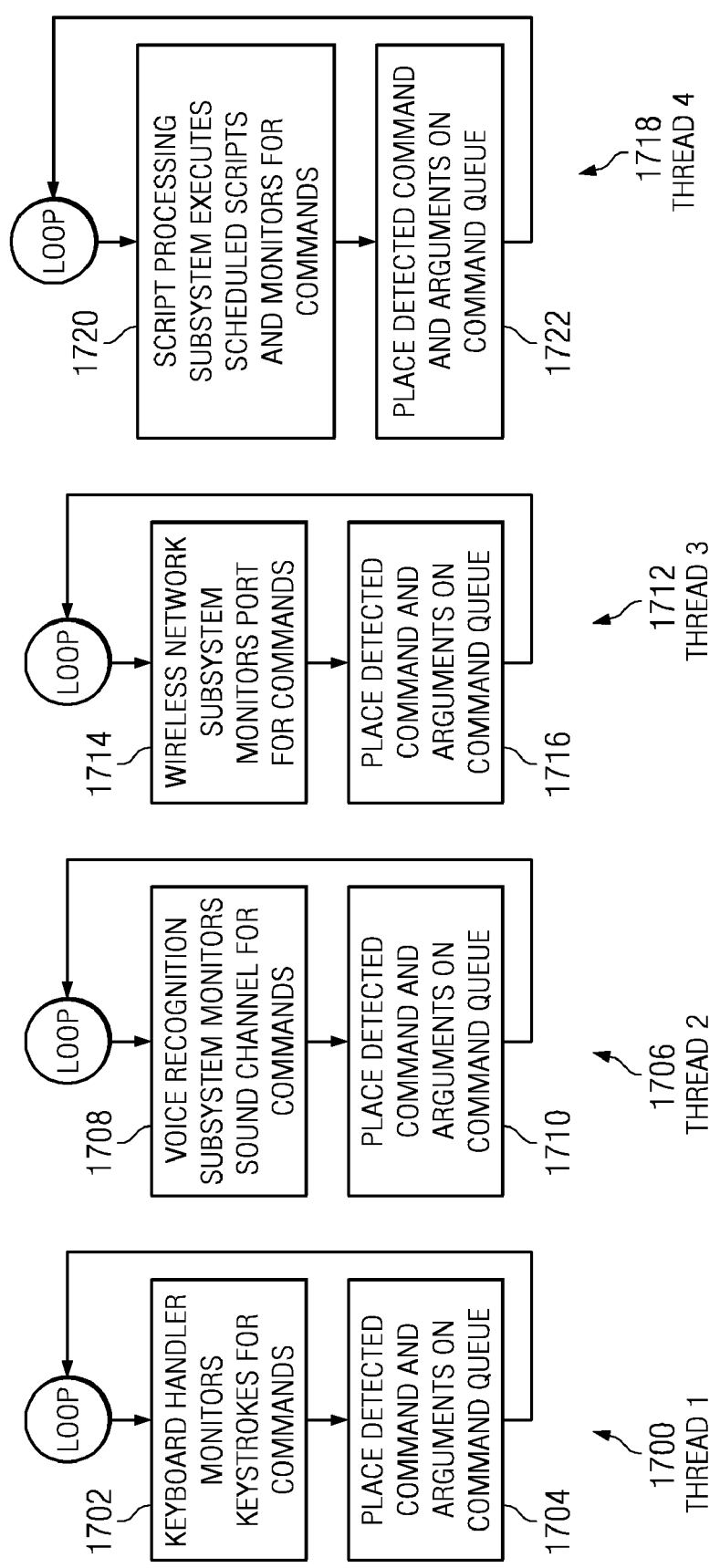
FIG. 17 illustrates different processes for adding commands to a command queue in accordance with an illustrative embodiment.

FIG. 17 is illustrates different processes for adding commands to a command queue in accordance with an illustrative embodiment. The processes illustrated in FIG. 17 may be implemented in a digital life recording system, such as digital life recording system 300 shown in FIG. 3.

In process 1700, a keyboard handler monitors keystrokes for commands (step 1702). In response to detecting a command, the detected command along with the associated arguments is placed on the command queue (step 1704). Process 1700 loops and continues monitoring (step 1702) and adding detected commands (step 1704) to the command queue.

In process 1706, a voice recognition subsystem monitors the sound channels for commands (step 1708). In response to detecting a command, the detected command along with the associated arguments is placed on the command queue (step 1710). Process 1706 loops and continues monitoring (step 1708) and adding detected commands (step 1710) to the command queue.

In process 1712, a wireless network subsystem monitors the ports for commands (step 1714). In response to detecting a command, the detected command along with the associated arguments is placed on the command queue (step 1716).

Process 1712 loops and continues monitoring (step 1714) and adding detected commands (step 1716) to the command queue.

In process 1718, a script processing subsystem executes scheduled scripts and monitors for commands (step 1720). In response to detecting a command, the detected command along with the associated arguments is placed on the command queue (step 1722). Process 1718 loops and continues monitoring (step 1720) and adding detected commands (step 1722) to the command queue.

Figure 18:
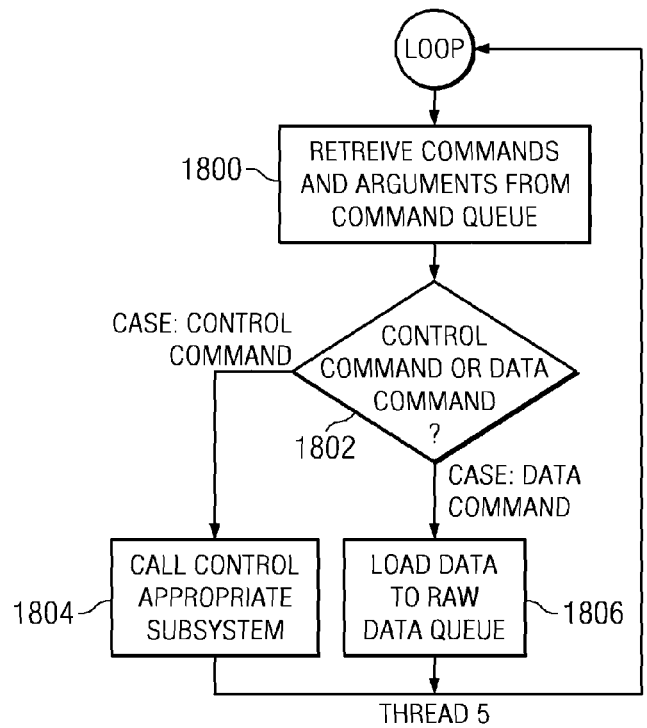
FIG. 18 is a flowchart illustrating a process for processing commands in accordance with an illustrative embodiment.

With reference to FIG. 18, a flowchart a process for processing commands is depicted in accordance with an illustrative embodiment. The process illustrated in FIG. 18 may be implemented in a digital life recording system, such as digital life recording system 300 shown in FIG. 3.

The process begins by retrieving commands and their associated arguments from a command queue (step 1800), such as command queue 512 shown in FIG. 5. The process interprets the retrieved command to determine if the retrieved command is a control command or a data command (step 1802). A control command is a command that modifies the operation of the digital life recording system. A data command is command request to select data associated with the digital life recording system.

In response to determining that the retrieved command is a control command, the process calls the control appropriate subsystem for processing the command (step 1804). In response to determining that the retrieved command is a data command, the process loads selected data to the raw data queue (step 1806). The process loops and repeats steps 1800-1806 for all commands in the command queue.

Figure 19:
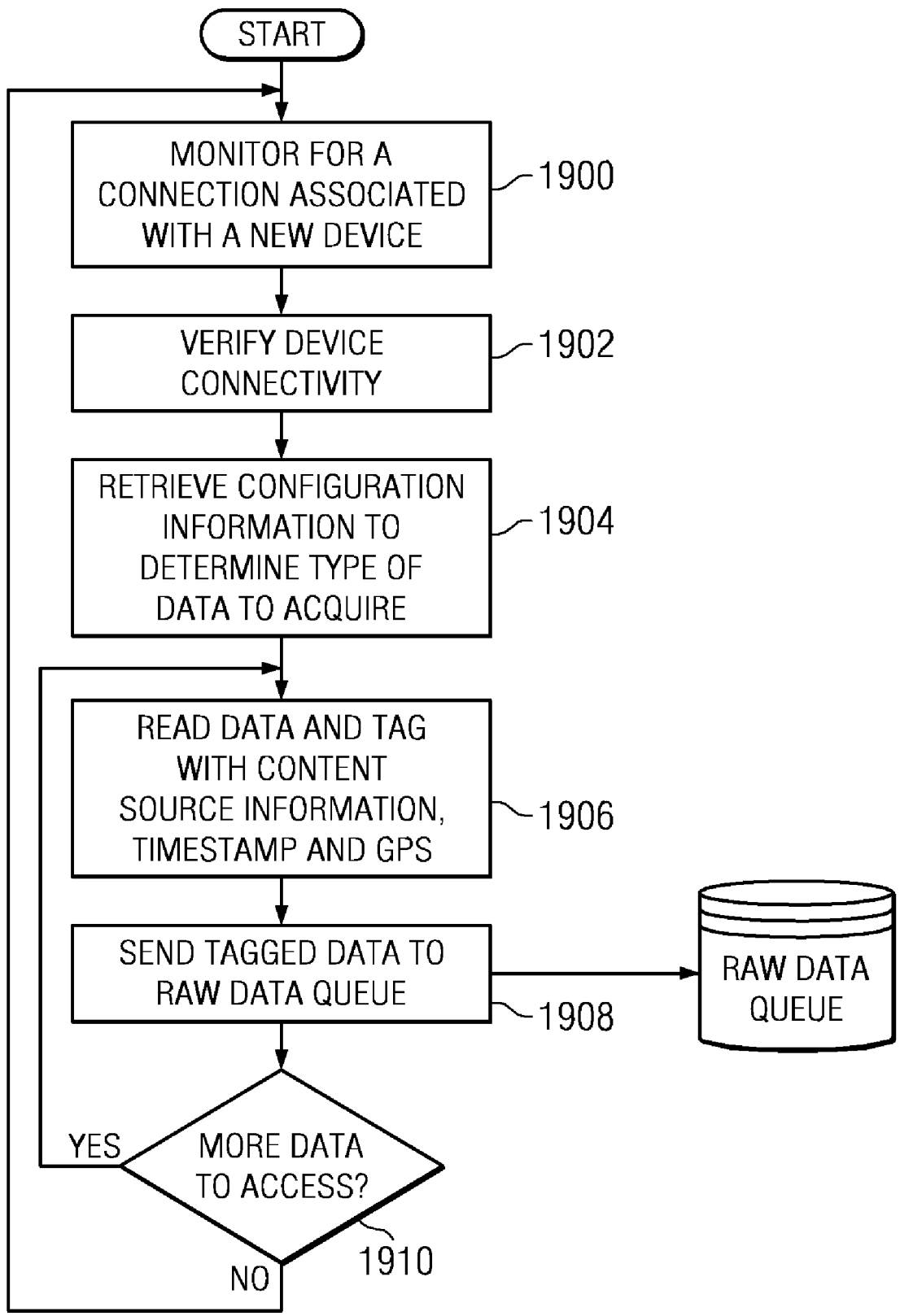
FIG. 19 is a flowchart illustrating a process for acquiring and organizing personal device data in accordance with an illustrative embodiment.

With reference to FIG. 19, a flowchart illustrating a process for acquiring and organizing personal device data is depicted in accordance with an illustrative embodiment. The process illustrated in FIG. 19 may be implemented in a digital life recording system, such as digital life recording system 300 shown in FIG. 3.

The process begins by monitoring for a connection associated with a new device (step 1900). The connection may be established either wirelessly, such as, but not limited to, Bluetooth enabled devices, or the connection may be established through a physical connection, such as, but not limited to, universal serial bus (USB) devices. The devices may include, but are not limited to, cellular phones, personal digital assistants (PDAs), and digital cameras. Responsive to detecting a connection, the process verifies the device connectivity (step 1902).

The process retrieves configuration information to determine the type of data to acquire from the connected device (step 1904). The process then reads data from the connected device(s) and tags the data with the content source information, a timestamp and global positioning system location (step 1906). The process sends the tagged data to the raw data queue (step 1908). The process determines whether more data exists in the connected device (step 1910). In response to a determination that more data exists in the connected device, the process repeats the steps of reading and tagging the data (step 1906), and sending the tagged data to the raw data queue (step 1908). In response to a determination that more data does not exist in the connected device, the process returns to the step of monitoring for a connection associated with a new device (step 1900).

Figure 20:
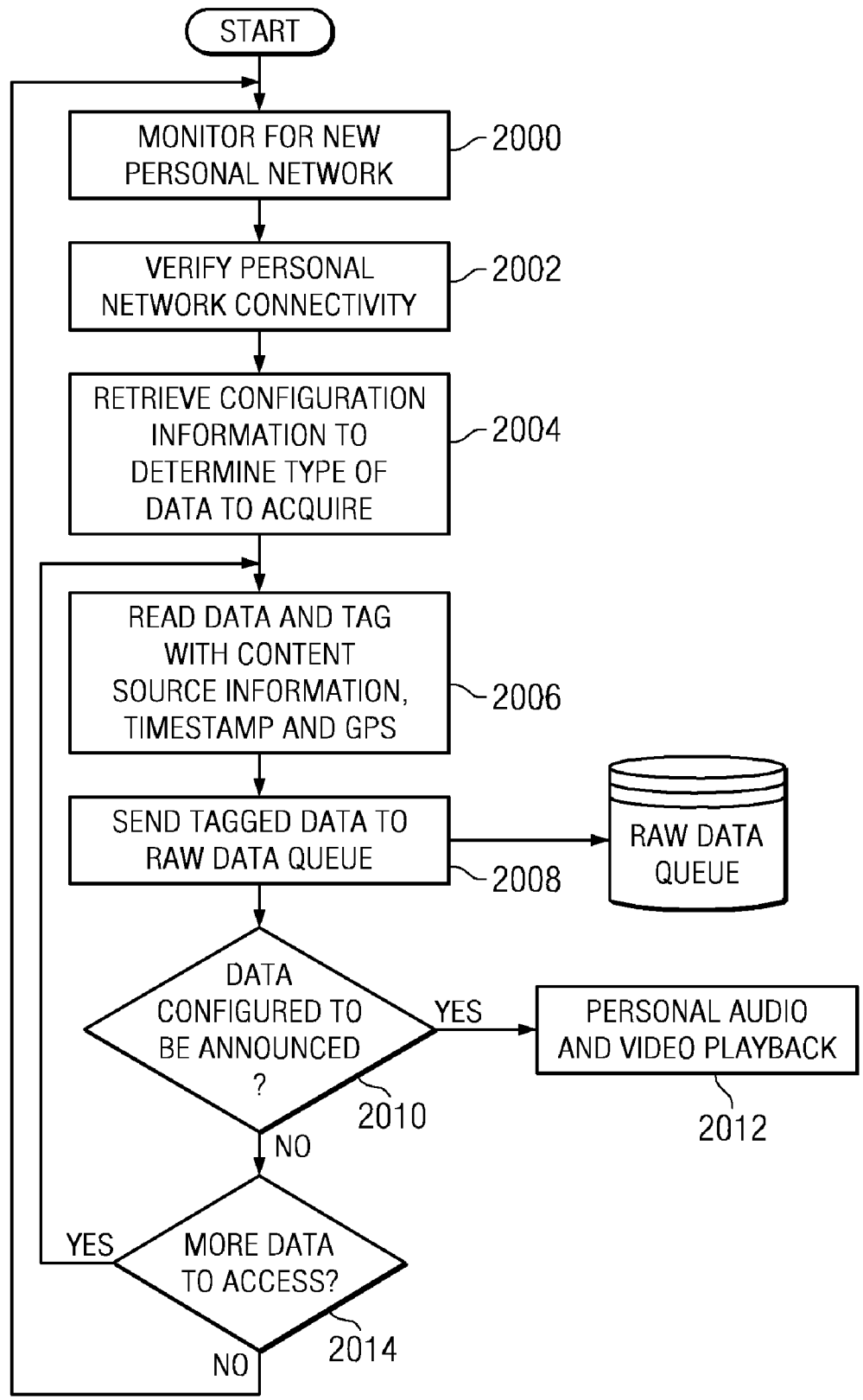
FIG. 20 is a flowchart illustrating a process for acquiring and organizing personal network data in accordance with an illustrative embodiment.

FIG. 20 is a flowchart of a process for acquiring and organizing personal network data in accordance with an illustrative embodiment. The process illustrated in FIG. 20 may be implemented in a digital life recording system, such as digital life recording system 300 shown in FIG. 3.

The process begins by monitoring for a connection associated with a new personal network (step 2000). The connection may be established either by wired or wireless means. In response to detecting a connection, the process verifies the personal network connectivity (step 2002). The process retrieves configuration information to determine the type of data to acquire from the connected personal network (step 2004).

The process then reads data from the connected personal network and tags the data with the content source information, a timestamp and global positioning system location (step 2006). The process sends the tagged data to the raw data queue (step 2008).

The process determines whether the data is configured to be announced (step 2010). Responsive to a determination that the data is configured to be announced, the data is forwarded to a personal audio and video playback subsystem for announcing the data to the person (step 2012). The process determines whether more data exists in the connected personal network (step 2014).

In response to a determination that more data exists in the connected personal network, the process repeats the steps of reading and tagging the data (step 2006), sending the tagged data to the raw data queue (step 2008), and determining whether the data is configured to be announced (step 2010). In response to a determination that more data does not exist in the connected personal network, the process returns to the step of monitoring for a connection associated with a new personal network (step 2000).

Figure 21:
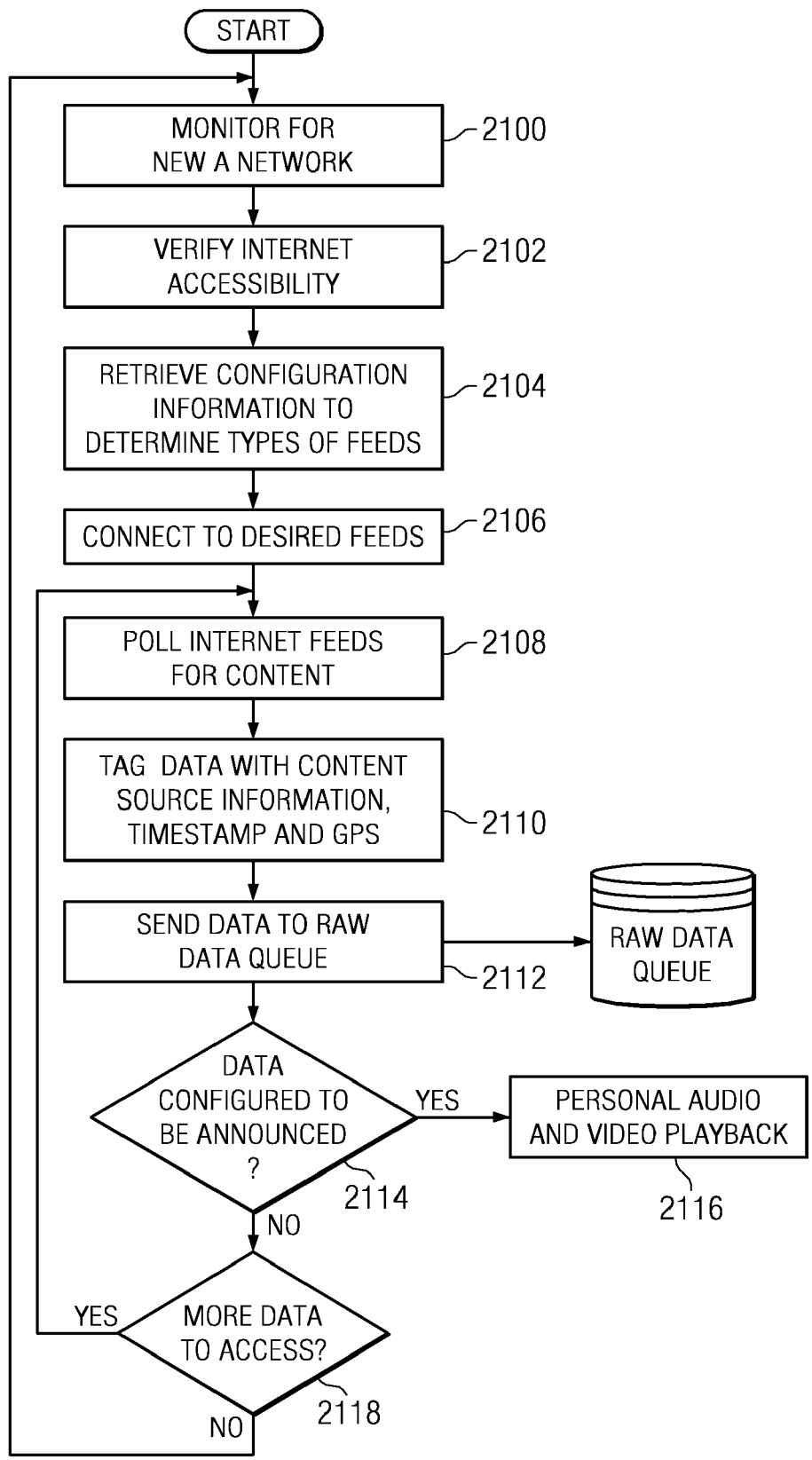
FIG. 21 is a flowchart illustrating a process for acquiring and organizing data from the internet in accordance with an illustrative embodiment.

FIG. 21 is a flowchart of a process for acquiring and organizing data from the Internet in accordance with an illustrative embodiment. The process illustrated in FIG. 21 may be implemented in a digital life recording system, such as digital life recording system 300 shown in FIG. 3.

The process begins by monitoring for a connection associated with a new network (step 2100). The connection may be established either by wired or wireless means. In response to detecting a connection, the process verifies internet accessibility (step 2102). The process then retrieves configuration information to determine the types of feeds to acquire (step 2104). A feed is data created by a party and broadcast over the internet to others. The process connects to the desired feeds (step 2106) and polls the internet feeds for content (step 2108). In response to receiving data/content from the internet feeds, the data is tagged with the content source information, a timestamp and global positioning system location (step 2110). The process sends the tagged data to the raw data queue (step 2112).

The process determines whether the data is configured to be announced (step 2114). Responsive to a determination that the data is configured to be announced, the data is forwarded to a personal audio and video playback subsystem for announcing the data to the person (step 2116). The process determines whether more data exists in the connected internet feeds (step 2112).

In response to a determination that more data exist in the connected internet feeds, the process repeats the steps of polling (step 2108) and tagging the data (step 2110), sending the tagged data to the raw data queue (step 2112), and determining whether the data is configured to be announced (step 2114). In response to a determination that more data does not exist in the connected internet feeds, the process returns to the step of monitoring for a connection associated with a new network (step 2100).

Figure 22:
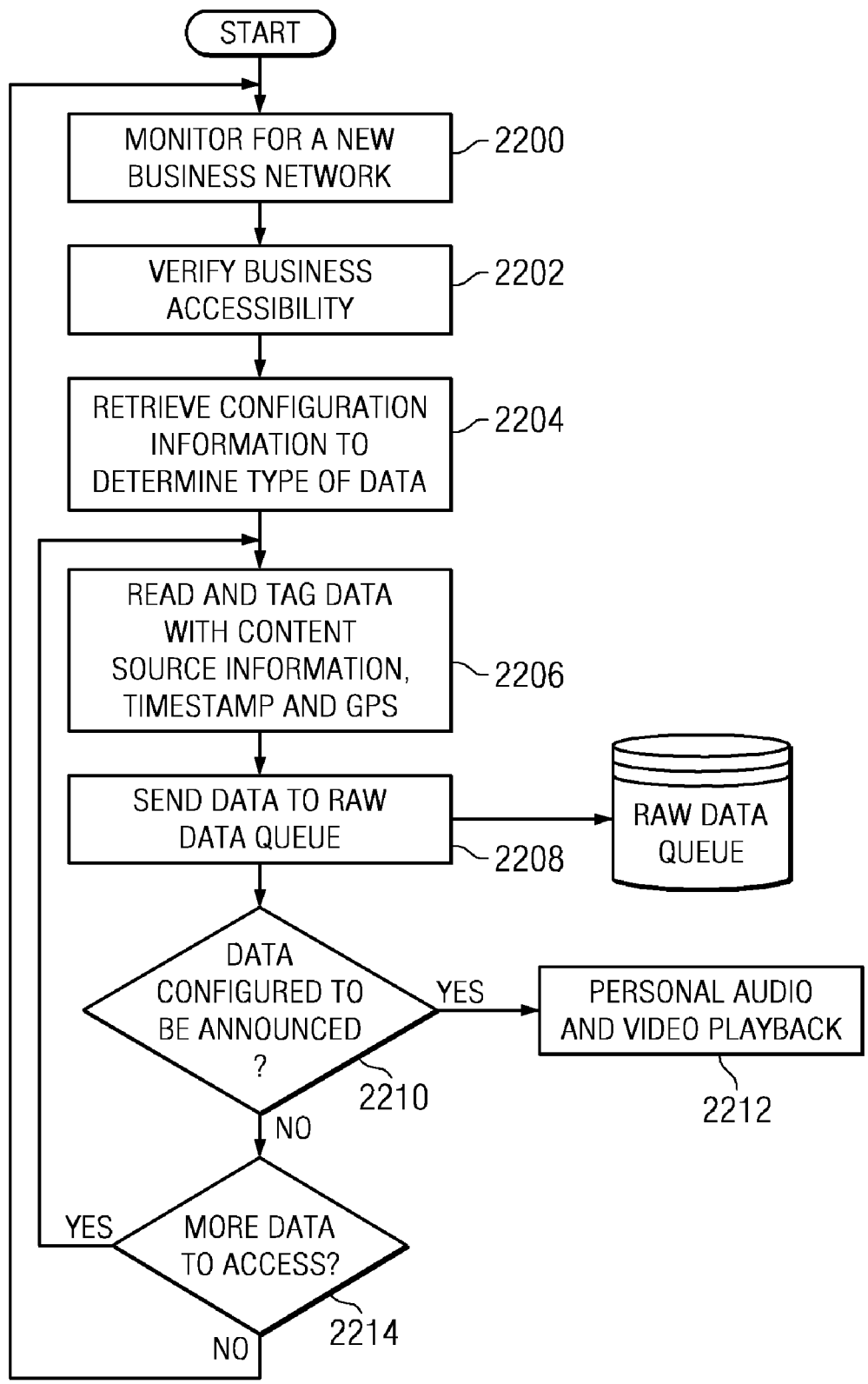
FIG. 22 is a flowchart illustrating a process for acquiring and organizing data from business networks in accordance with an illustrative embodiment.

FIG. 22 is a flowchart of a process for acquiring and organizing data from business networks in accordance with an illustrative embodiment. The process illustrated in FIG. 22 may be implemented in a digital life recording system, such as digital life recording system 300 shown in FIG. 3.

The process begins by monitoring for a connection associated with a new business network (step 2200). The connection may be established either by wired or wireless means. In response to detecting a connection, the process verifies the business network connectivity (step 2202). The process retrieves configuration information to determine the type of data to acquire from the connected business network (step 2204). The process then reads data from the connected business network and tags the data with the content source information, a timestamp and global positioning system location (step 2206). The process sends the tagged data to the raw data queue (step 2208).

The process determines whether the data is configured to be announced (step 2210). Responsive to a determination that the data is configured to be announced, the data is forwarded to a personal audio and video playback subsystem for announcing the data to the person (step 2212). The process determines whether more data exist in the connected business network (step 2214).

In response to a determination that more data exists in the connected business network, the process repeats the steps of reading and tagging the data (step 2206), sending the tagged data to the raw data queue (step 2208), and determining whether the data is configured to be announced (step 2210). In response to a determination that more data does not exist in the connected business network, the process returns to the step of monitoring for a connection associated with a new business network (step 2200).

Figure 23:
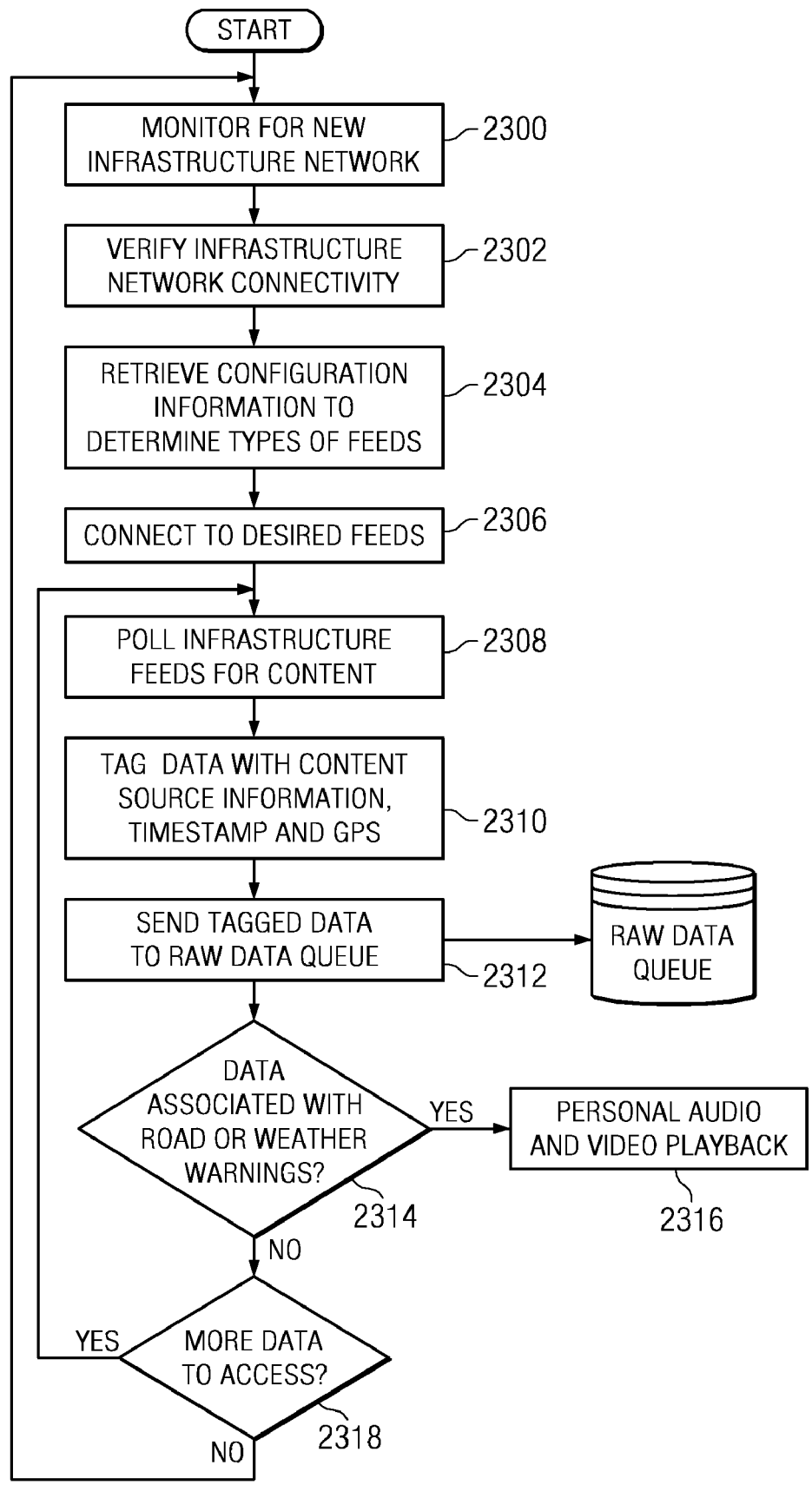
FIG. 23 is a flowchart illustrating a process for acquiring and organizing data from infrastructure networks in accordance with an illustrative embodiment.

FIG. 23 is a flowchart of a process for acquiring and organizing data from infrastructure networks in accordance with an illustrative embodiment. The process illustrated in FIG. 23 may be implemented in a digital life recording system, such as digital life recording system 300 shown in FIG. 3.

The process begins by monitoring for a connection associated with a new infrastructure network (step 2300). The connection may be established either by wired or wireless means. In response to detecting a connection, the process verifies infrastructure network connectivity (step 2302). The process then retrieves configuration information to determine the types of feeds to acquire (step 2304). The types of feeds may include, but are not limited to, feeds containing data associated with weather conditions and feeds containing data associated with road conditions.

The process connects to the desired feeds (step 2306) and polls the infrastructure feeds for content (step 2308). In response to receiving data/content from the infrastructure feeds, the data is tagged with the content source information, a timestamp and global positioning system location (step 2310). The process sends the tagged data to the raw data queue (step 2312).

The process determines whether the retrieved data contains data associated with road warnings or weather warnings related to the current location of the person (step 2314). In response to a determination that the retrieved data contains data associated with road warnings or weather warnings related to the current location of the person, the road warning/weather warning is sent to a personal audio and video playback subsystem for announcing the warning(s) to the person (step 2316).

The process determines whether more data exists in the connected infrastructure feeds (step 2318). In response to a determination that more data exists in the connected infrastructure feeds, the process repeats the steps of polling (step 2308) and tagging the data (step 2310), sending the tagged data to the raw data queue (step 2312), and determining whether the data contains data associated with road warnings or weather warnings related to the current location of the person (step 2314).

In response to a determination that more data does not exist in the connected infrastructure feeds, the process returns to the step of monitoring for a connection associated with a new infrastructure network (step 2300).

Figure 24:
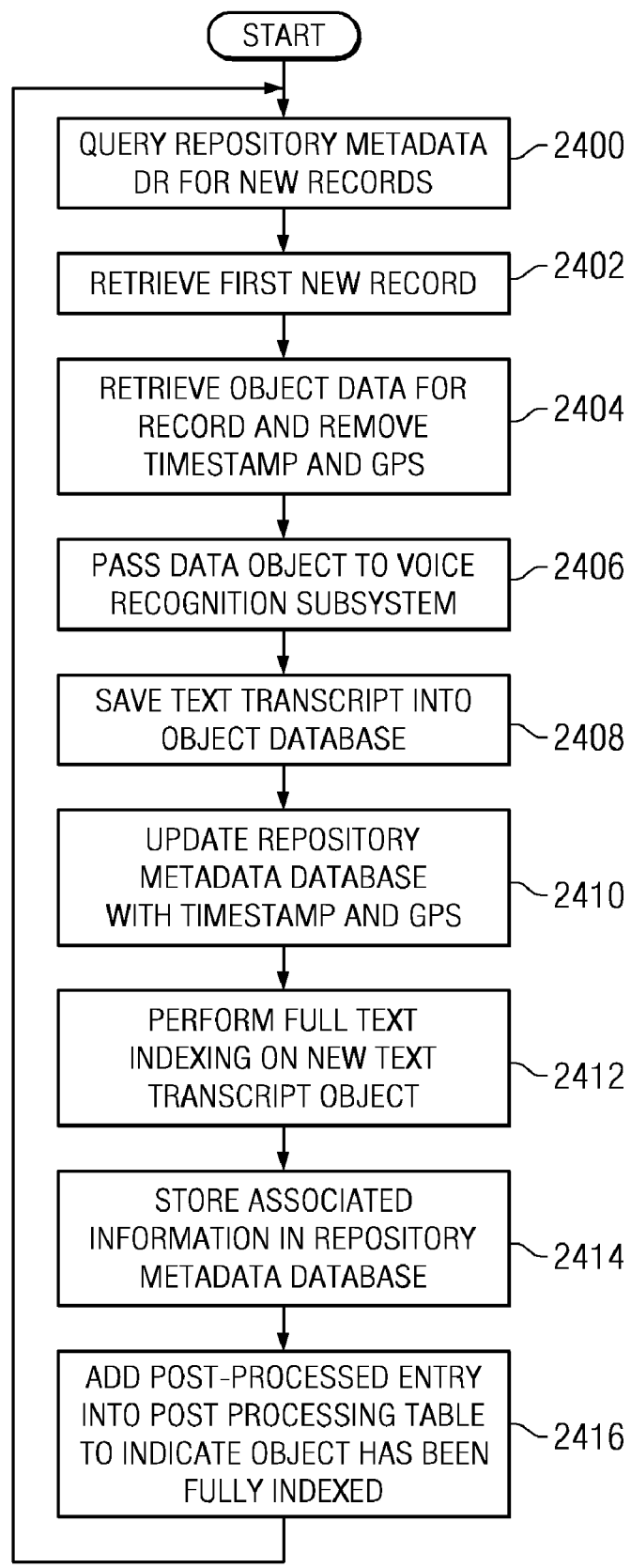
FIG. 24 is a flowchart illustrating a process for indexing data stored in the repository mass store in accordance with an illustrative embodiment.

With reference now to FIG. 24, a flowchart of a process for improving the indexing of data stored in the repository mass store is depicted in accordance with an illustrative embodiment. The process illustrated in FIG. 24 may be implemented in a digital life recording system, such as digital life recording system 300 shown in FIG. 3.

The process begins by querying a repository metadata database, such as digital life metadata database 538 shown in FIG. 5, for new records (step 2400). In response to a determination that new records exist, the process retrieves the first new record (step 2402). The process retrieves the object data associated with the new record and retrieves the global positioning system (GPS) timestamp and location from the object data (step 2404). The process passes the data object to a voice recognition subsystem to generate a text transcript of the object data. (step 2406).

The process saves the text transcript into an object database (step 2408), such as digital life information object database 540 shown in FIG. 5. The process then updates the repository metadata database with the global positioning system (GPS) timestamp and location, a unique identifier that points to the physical location of the text object (step 2410). The process then performs full text indexing on the new text transcript object (step 2412). The process stores the information associated with the full text indexing in the repository metadata database (step 2414). The process adds a post-processed entry, for the text transcript object, into a post processing table to indicate that the associated text transcript object has been fully indexed (step 2416). The process loops and queries the repository metadata database for a new record (step 2400).

Figure 25:
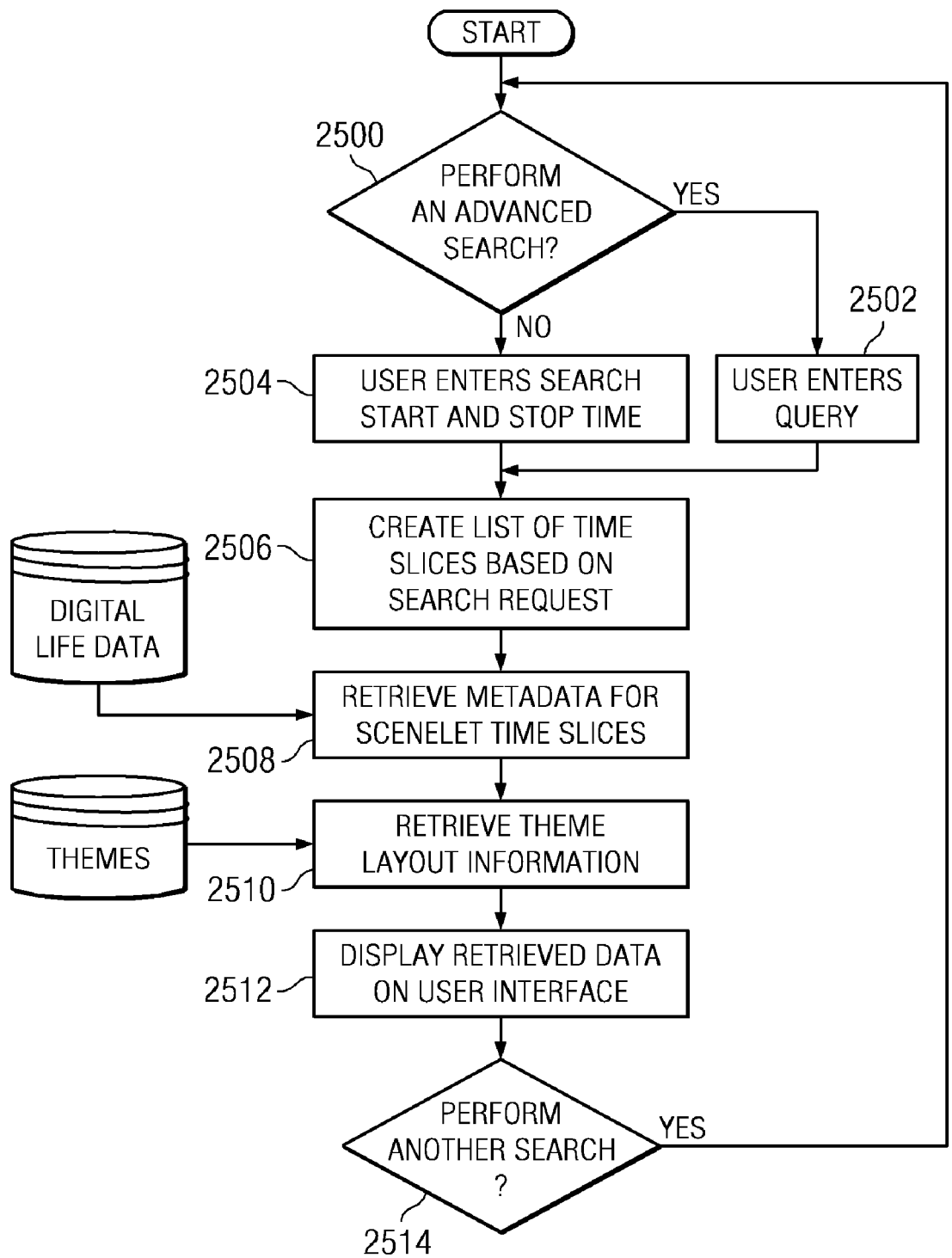
FIG. 25 is a flowchart illustrating a process for searching, retrieving, and rendering data in accordance with an illustrative embodiment.

With reference now to FIG. 25, a flowchart of a process for searching, retrieving, and rendering data is depicted in accordance with an illustrative embodiment. The process illustrated in FIG. 25 may be implemented in a digital life recording system, such as digital life recording system 300 shown in FIG. 3.

The process begins by determining whether the user has selected an option to perform an advance search (step 2500). In an advance search, the process receives a query request from a user to query the repository database (step 2502). The query uses a database querying language, such as, but not limited to, structured query language (SQL). For a regular search, the process receives a request from a user containing a starting date/time and an ending date/time (step 2504). The process creates a list of time slices based on the search request (step 2506).

The process retrieves metadata for the scenelet time slices from a digital life data repository (step 2508), such as digital life data repository 804 shown in FIG. 8. The process also retrieves metadata for non-video information, such as, but not limited to, audio and temperature. The process then retrieves theme layout information from a themes database (step 2510), such as themes database 818 shown in FIG. 8. The process displays the retrieved data on a user interface (step 2512), such as user interface 900 shown in FIG. 9. The process then determines whether another search request is to be performed (step 2514). In response to determining that another search request is to be performed, the process loops back to step 2500.

Figure 26:
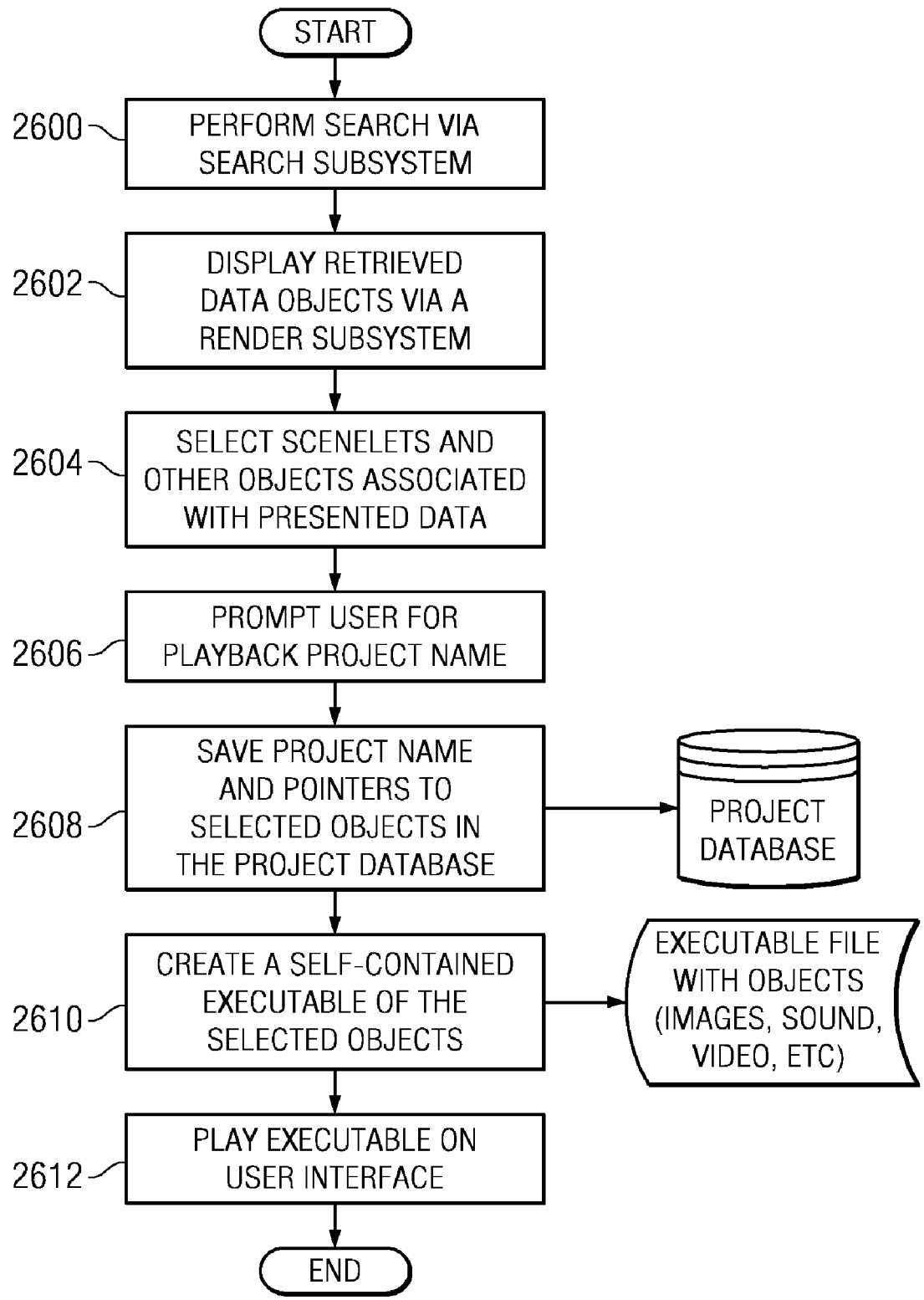
FIG. 26 is a flowchart illustrating a process for organizing and presenting data in accordance with an illustrative embodiment.

With reference now to FIG. 26, a flowchart of a process for organizing and presenting data is depicted in accordance with an illustrative embodiment. The process illustrated in FIG. 26 may be implemented in a digital life recording system, such as digital life recording system 300 shown in FIG. 3.

The process begins by performing a search for data objects via a search subsystem (step 2600), such as search subsystem 812 shown in FIG. 8. The process displays the retrieved data objects via a render subsystem (step 2602), such as render subsystem 814 shown in FIG. 8. The process selects scenelets and other objects associated with presented data (step 2604).

The process then prompts a user for a playback project name (step 2606). In response to receiving a project name from a user, the process saves the project name and pointers to the selected objects in a project definitions database (step 2608), such as project definitions database 858 shown in FIG. 8. A pointer is a variable that holds the address of a data object or function.

The process then creates a self-contained executable of the selected objects (step 2610). The self-contained executable may be emailed, posted to a web-site, or saved in non-volatile memory, such as on a hard drive. In response to a receiving a request to execute the self-contained executable of the selected objects, the process plays the self-contained executable on a user interface (step 2612), such as user interface 900 shown in FIG. 9.

Thus, the illustrative embodiments described herein provide a computer implemented method, apparatus, and computer program product for managing data. Data capturing devices dynamically capture data associated with the daily activities of a person. The data is processed using a mobile device associated with the person. The data is stored into a cache of the mobile device. The data stored in the cache of the mobile device is uploaded into a repository mass store in response to interfacing the mobile device with the repository mass store. A selected data segment stored in the repository mass store is presented in response to receiving a request for the selected data segment.

The illustrative embodiments dynamically capture all aspects of daily activities associated with a person using a plurality of data capturing devices. Additionally, the illustrative embodiments captures data from external sources, such as, but not limited to, other people's life data recording system, public and private internet feeds, and information captured from broadcasts associated with businesses. Furthermore, the illustrative embodiments capture biometric data associated with the person including, but not limited to, temperature, heart rate, and blood pressure.

The illustrative embodiments present methods for capturing, organizing, and presenting the data in an efficient method. A person is able to digitally save all or any aspect and/or experience of the person's life for future viewing. Additionally, the data can be shared with other people, such as friends and family, or be archived for future generations to experience.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method for managing digital life recording data, the computer implemented method comprising:

capturing data associated with daily activities of a first person using a plurality of data capturing devices associated with a first mobile digital life recording device associated with the first person to form captured data, wherein the captured data includes sound data, and video data;

processing the captured data using the first mobile digital life recording device wherein processing the captured data comprises:

organizing the sound data and the video data into a plurality of data segments; and tagging each data segment within the plurality of data segments with a global positioning system location identifier and a timestamp;

storing the plurality of data segments into a cache of the first mobile digital life recording device; and sending a portion of the plurality of data segments to a second mobile digital life recording device associated with a second person that is authorized by the first person to receive the portion of the plurality of data segments via a wireless network, wherein the plurality of data segments stored in the cache of the mobile device further comprises data retrieved from an information source over a wireless network, and wherein the information source is the second mobile digital life recording device associated with the second person;

responsive to interfacing the first mobile digital life recording device with a repository mass store, uploading and storing the plurality of data segments stored in the cache of the first mobile digital life recording device and data segments received from the second person of the second mobile digital life recording device into the repository mass store to form a plurality of uploaded data segments;

processing the plurality of uploaded data segments stored at the repository mass store, wherein processing the plurality of uploaded data segments comprises:

generating a text transcript of the sound data and a plurality of thumbnail images for the video data for each data segment within the plurality of uploaded data segments;

generating metadata associated with terms in the text transcript;

indexing each data segment within the plurality of uploaded data segments based on the global positioning system location identifier, the timestamp, and the text transcript; and indexing the sound data in the plurality of uploaded data segments based on the metadata from the text transcript; and responsive to receiving a request to view data within a selected period of time, presenting the sound data, the video data, the plurality of thumbnail images, and the text transcript for each data segment within the plurality of uploaded data segments stored at the repository mass store within the selected period of time using a user interface.

2. The computer implemented method of claim 1, wherein indexing each data segment within the plurality uploaded of data segments further comprises:

indexing additional metadata associated with a data segment of the plurality of uploaded data segments into an indexing database, wherein the additional metadata describes the content, quality, condition, and origin of the data segment.

3. The computer implemented method of claim 1, wherein the plurality of data capturing devices comprises of a set of video capturing devices, a set of audio capturing devices, a set of biometric capturing devices, a set of global positioning devices, and a set of environmental sensor devices.

4. The computer implemented method of claim 1, wherein processing the plurality of uploaded data segments comprises:

identifying at least one known human contact other than the first person in a number of uploaded data segments of the plurality of uploaded data segments;

wherein indexing each data segment within the plurality of uploaded data segments further comprises:

indexing each data segment within the plurality of uploaded data segments based on the at least one known human contact other than the first person in the number of uploaded data segments of the plurality of uploaded data segments.

5. The computer implemented method of claim 4, further comprising:

extracting a voice command from the plurality of data segments using a speech recognition filter; and executing a function associated with the voice command.

6. The computer implemented method of claim 5, wherein the voice command specifies a tagging operation and a text index that is associated with a data segment within the plurality of data segments.

7. The computer implemented method of claim 1, further comprising:

responsive to storing the plurality of data segments into the cache of the mobile device to form collected data, presenting the plurality of data segments to the person using a monitoring device.

8. The computer implemented method of claim 1, wherein uploading the plurality of data segments comprises:

processing the plurality of data segments stored in the cache of the mobile device prior to storing the plurality of data segments into the repository mass store.

9. The computer implemented method of claim 1, further comprising:

extracting a command from a script; and executing functions associated with the command.

10. The computer implemented method of claim 1, wherein the plurality of data capturing devices captures a 360 degree field of view around the person.

11. The computer implemented method of claim 1, wherein at least one of the plurality of data capturing devices is embedded in the person.

12. The computer implemented method of claim 1, wherein the information source is an internet source.

13. A computer program product comprising:

a computer recordable storage medium including computer usable program code for managing digital life recording data, said computer program product comprising:

computer usable program code for capturing data associated with daily activities of a first person using a plurality of data capturing devices associated with a first mobile digital life recording device associated with the first person to form captured data, wherein the captured data includes sound data, and video data;

computer usable program code for processing the captured data using the first mobile digital life recording device, wherein the computer usable program code for processing the captured data comprises:

computer usable program code for organizing the sound data and the video data into a plurality of data segments;

computer usable program code for tagging each data segment within the plurality of data segments with a global positioning system location identifier and a timestamp;

computer usable program code for storing the plurality of data segments into a cache of the first mobile digital life recording device;

computer usable program code for sending a portion of the plurality of data segments to a second mobile digital life recording device associated with a second person that is authorized by the first person to receive the portion of the plurality of data segments via a wireless network, wherein the plurality of data segments stored in the cache of the mobile device further comprises data retrieved from an information source over a wireless network, and wherein the information source is the second mobile digital life recording device associated with the second person;

computer usable program code for uploading and storing the plurality of data segments stored in the cache of the first mobile digital life recording device and data segments received from the second person of the second mobile digital life recording device into a repository mass store to form a plurality of uploaded data segments in response to interfacing the first mobile digital life recording device with the repository mass store;

computer usable program code for processing the plurality of uploaded data segments stored at the repository mass store, wherein the computer usable program code for processing the plurality of uploaded data segments comprises:

computer usable program code for generating a text transcript of the sound data a plurality of thumbnail images for and the video data for each data segment within the plurality of uploaded data segments;

computer usable program code for generating metadata associated with terms in the text transcript;

computer usable program code for indexing each data segment within the plurality of uploaded data segments based on the global positioning system location identifier, the timestamp, and the text transcript; and computer usable program code for indexing the sound data in the plurality of uploaded data segments based on the metadata from the text transcript; and computer usable program code for presenting the sound data, the video data, the plurality of thumbnail images, and the text transcript for each data segment within the plurality of uploaded data segments stored at the repository mass store within a selected period of time using a user interface in response to receiving a request to view data within the selected period of time.

14. The computer program product of claim 13, wherein the computer usable program code for indexing each data segment within the plurality of uploaded data segments further comprises:

computer usable program code for indexing additional metadata associated with a data segment of the plurality of uploaded data segments into an indexing database, wherein the additional metadata describes the content, quality, condition, and origin of the data segment.

15. The computer program product of claim 13, wherein the plurality of data capturing devices comprises of a set of video capturing devices, a set of audio capturing devices, a set of biometric capturing devices, a set of global positioning devices, and a set of environmental sensor devices.

16. A digital life recording system comprising:

a plurality of data capturing devices associated with a first mobile digital life recording device associated with a first person, the plurality of data capturing devices configured to capture data associated with daily activities of a first person to form captured data, wherein the captured data includes sound data, and video data;

a first mobile digital life recording device associated with the first person configured to process and store the captured data to form stored data, wherein the first mobile digital life recording device organizes the sound data and the video data into a plurality of data segments; tags each data segment within the plurality of data segments with a global positioning system location identifier and a timestamp; store the plurality of data segments into a cache of the first mobile digital life recording device; and send a portion of the plurality of data segments to a second mobile digital life recording device associated with a second person that is authorized by the first person to receive the portion of the plurality of data segments via a wireless network, wherein the plurality of data segments stored in the cache of the mobile device further comprises data retrieved from an information source over a wireless network, and wherein the information source is the second mobile digital life recording device associated with the second person;

a storage device configured to receive and store the plurality of data segments stored in the cache of the first mobile digital life recording device and data segments received from the second person of the second mobile digital life recording device into the repository mass store to form a plurality of uploaded data segments in response to interfacing the first mobile digital life recording device with the storage device;

a data processing system configured to process the plurality of uploaded data segments stored at the storage device; generate a text transcript of the sound data and a plurality of thumbnail images for the video data for each data segment within the plurality of data segments; generate metadata associated with terms in the text transcript; index each data segment within the plurality of uploaded data segments based on the global positioning system location identifier, the timestamp, and the text transcript; index the sound data in the plurality of uploaded data segments based on the metadata from the text transcript; and retrieve and present the sound data, the video data, the plurality of thumbnail images, and the text transcript for each data segment within the plurality of uploaded data segments stored on the storage device within the selected period of time to a user in response to receiving a request to view data within a selected period of time.

17. An apparatus comprising:

a bus system;

a communications system connected to the bus system;

a memory connected to the bus system, wherein the memory includes computer usable program code; and a process unit connected to the bus system, wherein the process unit executes the computer usable program code to capture data associated with daily activities of a first person using a plurality of data capturing devices associated with a first mobile digital life recording device associated with the first person to form captured data, wherein the captured data includes sound data, and video data; process the captured data using the first mobile digital life recording device, wherein processing the captured data comprises: organizing the sound data and the video data into a plurality of data segments; tagging each data segment within the plurality of data segments with a global positioning system location identifier and a timestamp; storing the plurality of data segments into a cache of the first mobile digital life recording device; and sending a portion of the plurality of data segments to a second mobile digital life recording device associated with a second person that is authorized by the first person to receive the portion of the plurality of data segments via a wireless network, wherein the plurality of data segments stored in the cache of the mobile device further comprises data retrieved from an information source over a wireless network, and wherein the information source is the second mobile digital life recording device associated with the second person; upload and store the plurality of data segments stored in the cache of the first mobile digital life recording device and data segments received from the second person of the second mobile digital life recording device into the repository mass store to form a plurality of uploaded data segments in response to interfacing the first mobile digital life recording device with a repository mass store; process the plurality of uploaded data segments stored at the repository mass store, wherein processing the plurality of uploaded data segments comprises: generating a text transcript of the sound data and a plurality of thumbnail images for the video data for each data segment within the plurality of uploaded data segments; generating metadata associated with terms in the text transcript; indexing each data segment within the plurality of uploaded data segments based on the global positioning system location identifier, the timestamp, and the text transcript; and indexing the sound data in the plurality of uploaded data segments based on the metadata from the text transcript; and present the sound data, the video data, the plurality of thumbnail images, and the text transcript for each data segment within the plurality of uploaded data segments stored at the repository mass store within a selected period of time using a user interface in response to receiving a request to view data within the selected period of time.

* * * * *